United States Patent [19]

Hakimi et al.

[11] Patent Number: 5,747,646
[45] Date of Patent: May 5, 1998

[54] POLYETHYLENE-PROTEIN CONJUGATES

[75] Inventors: John Hakimi, Scarsdale; Patricia Kilian, Upper Montclair; Perry Rosen, North Caldwell, all of N.J.

[73] Assignee: Hoffmann-La Roche Inc., Nutley, N.J.

[21] Appl. No.: 457,058

[22] Filed: Jun. 1, 1995

Related U.S. Application Data

[60] Division of Ser. No. 767,000, Sep. 27, 1991, Pat. No. 5,595,732, which is a continuation-in-part of Ser. No. 674,001, Mar. 25, 1991, abandoned.

[51] Int. Cl.$^6$ .............. C07K 1/00; A61K 38/19; A61K 38/21
[52] U.S. Cl. .......... 530/351; 424/85.4; 424/85.1; 424/85.2; 424/85.7; 530/350; 530/403; 530/405; 530/409; 564/23; 435/188
[58] Field of Search .............. 564/23; 530/350, 530/351, 403, 405, 409, 408; 424/85.1, 85.2, 85.4, 85.7; 435/188

[56] References Cited

U.S. PATENT DOCUMENTS

| | | |
|---|---|---|
| 3,607,653 | 9/1971 | Ziffer et al. . |
| 3,619,371 | 11/1971 | Crook et al. . |
| 3,639,213 | 2/1972 | Ginger et al. . |
| 3,645,852 | 2/1972 | Axen et al. . |
| 3,788,948 | 1/1974 | Kagedal et al. . |
| 3,959,080 | 5/1976 | Orth et al. ............... 195/63 |
| 4,002,531 | 1/1977 | Royer . |
| 4,094,744 | 6/1978 | Hartdegen et al. ......... 530/816 |
| 4,100,271 | 7/1978 | Krezanoski . |
| 4,179,337 | 12/1979 | Davis et al. . |
| 4,261,973 | 4/1981 | Lee et al. . |
| 4,275,000 | 6/1981 | Ross . |
| 4,301,144 | 11/1981 | Iwashita et al. . |
| 4,310,397 | 1/1982 | Kaetsu et al. . |
| 4,486,364 | 12/1984 | Bucker ............... 530/409 |
| 4,496,689 | 1/1985 | Mitra ............... 525/54.1 |
| 4,609,546 | 9/1986 | Hirotani . |
| 4,640,835 | 2/1987 | Shimizu et al. . |
| 4,704,274 | 11/1987 | Sakuma et al. . |
| 4,732,863 | 3/1988 | Tomasi et al. . |
| 4,766,106 | 8/1988 | Katre et al. . |
| 4,791,192 | 12/1988 | Nakagawa et al. . |
| 4,797,491 | 1/1989 | Nitecki et al. ............... 546/291 |
| 4,810,638 | 3/1989 | Albarella et al. . |
| 4,818,769 | 4/1989 | Nunberg et al. . |
| 4,847,079 | 7/1989 | Kwan . |
| 4,847,325 | 7/1989 | Shadle et al. ............... 525/54.1 |
| 4,851,220 | 7/1989 | Yim et al. . |
| 4,871,538 | 10/1989 | Yim et al. . |
| 4,894,226 | 1/1990 | Aldwin et al. . |
| 4,902,502 | 2/1990 | Nitecki et al. ............... 424/83 |
| 4,917,888 | 4/1990 | Katre et al. . |
| 4,935,465 | 6/1990 | Garman . |
| 5,034,514 | 7/1991 | Nitecki et al. ............... 530/391.1 |
| 5,089,261 | 2/1992 | Nitecki et al. ............... 424/85.2 |
| 5,100,664 | 3/1992 | Doyle et al. . |
| 5,102,872 | 4/1992 | Singh et al. . |
| 5,122,614 | 6/1992 | Zalipsky . |
| 5,214,131 | 5/1993 | Sano et al. ............... 530/345 |
| 5,539,063 | 7/1996 | Hakimi et al. ............... 525/403 |
| 5,559,213 | 9/1996 | Hakimi et al. ............... 530/351 |

FOREIGN PATENT DOCUMENTS

| | | |
|---|---|---|
| 0154316 | 9/1985 | European Pat. Off. . |
| 304 311 | 2/1989 | European Pat. Off. . |
| 87/00056 | 1/1987 | WIPO . |
| 906 546 | 7/1989 | WIPO . |
| 004 606 | 5/1990 | WIPO . |
| 005 534 | 5/1990 | WIPO . |
| 007 938 | 7/1990 | WIPO . |
| 90/13540 | 11/1990 | WIPO . |
| 107 190 | 5/1991 | WIPO . |
| 108 229 | 6/1991 | WIPO . |

OTHER PUBLICATIONS

Veronese, Applied Biochem. & Biotechnolo. 11:141–152 (1985).
Arend et al., J. Clin. Invest. 88:1694–1697 (1990).
Knauf et al., J. Biological. Chem. 263:15064–15070 (1988).
Ho et al., Drug Metab. and Disposition 14:349–352 (1986).
King et al., Int. Archs. Allergy Appl. Immun. 66:439–446 (1981).
Nureddin et al., Biochem. J. 147:71–81 (1975).
Abuchoski et al., Biochem. Biophys. 7:175–186 (1984).
Eisenberg et al., Nature 343:341–346 (1990).
Ohlsson et al., Nature 348:550–552 (1990).
King et al., Int. Archs. Allergy Appl. Immun. 66:439–446 (1981).
Szego et al., Chem. Abs. 101:700 Abstact No. 13059m (1984).
Katre et al., Proc. Natl. Acad. Sci, vol. 84, pp. 1487–1491, Mar. 1987.
Zalipsky et al (1986) Polym. Prep. 27(1):1–2.
King et al (1980) Int. J. Protein Peptide Res. 16:147–155.

*Primary Examiner*—Chhaya D. Sayala
*Attorney, Agent, or Firm*—George W. Johnston; William H. Epstein; Lewis J. Kreisler

[57] ABSTRACT

The present invention is a physiologically active, substantially non-immunogenic water soluble polyethylene glycol protein conjugate having the same utility as the protein which forms the conjugate, without having the same properties of producing an immunogenic response possessed by the protein which forms this conjugate.

12 Claims, No Drawings

POLYETHYLENE-PROTEIN CONJUGATES

This is a division, of application Ser. No. 07/767,000, filed Sep.27,1991, U.S. Pat. No. 5595732 which in turn is a contiuation-in-part of Ser. No. 07/674,001, filed Mar. 25, 1991 abandoned.

BACKGROUND OF THE INVENTION

Various natural and recombinant proteins have medical and pharmaceutical utility. Once they have been purified, separated, and formulated, they can be parenterally administered for various therapeutic indications. However, parenterally administered proteins may be immunogenic, may be relatively water insoluble, and may have a short pharmacological half life. Consequently, it can be difficult to achieve therapeutically useful blood levels of the proteins in patients.

These problems may be overcome by conjugating the proteins to polymers such as polyethylene glycol. Davis et al., U.S. Pat. No. 4,179,337 disclose conjugating polyethylene glycol (PEG) to proteins such as enzymes and insulin in order to result in conjugates where the protein would be less immunogenic and would retain a substantial proportion of its physiological activity. Nakagawa, et al. disclose conjugating PEG to islet-activating protein to reduce its side-effects and immunogenicity. Veronese et al., Applied Biochem. and Biotech. 11:141–152 (1985) disclose activating polyethylene glycols with phenyl chloroformates to modify a ribonuclease and a superoxide dimutase. Katre et al. U.S. Pat. Nos. 4,766,106 and 4,917,888 also disclose solubilizing proteins by polymer conjugation. PEG and other polymers are conjugated to recombinant proteins to reduce immunogenicity and increase half-life. See Nitecki, et al., U.S. Pat. No. 4,902,502, Enzon, Inc., International Application No. PCT/US90/02133, Nishimura et al., European Patent Application 154,316 and Tomasi, International Application Number PCT/US85/02572.

Previous methods of forming PEG/Protein conjugates and the conjugates which result from said methods present several problems. Among these problems is that certain methods of forming these protein-PEG conjugates may inactivate the protein so that the resulting conjugates may have poor biological activity. In addition, certain linkers utilized in forming these PEG-protein conjugates may be susceptible to in vivo hydrolytic cleavage. When such cleavage occurs after administration, these conjugates lose the beneficial properties provided by PEG.

SUMMARY OF THE INVENTION

We have discovered that the problems associated with forming PEG-protein conjugates are circumvented by providing a novel PEG/Protein conjugate through the use of unique linkers which connect the various free amino groups in the protein to PEG.

The present invention is directed to physiologically active protein conjugates having the formula:

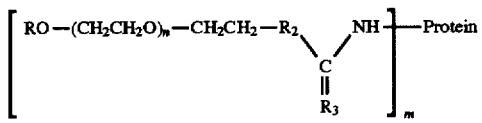

wherein R is lower alkyl; $R_2$ is —O— or —NH—; $R_3$ is =N—$R_4$, =S or =O; $R_4$ is a lower alkyl or cycloalkyl group and m and n are selected from any combination of numbers such that the conjugate has at least a portion of the biological activity of the protein which forms the conjugate; with the proviso that when $R_2$ is —O—; $R_3$ is =S.

In accordance with the present invention, we have also provided for the first time the protein Interleukin-1 receptor antagonist (IL-Ira) and Interleukin-1 (IL-1) conjugated to PEG.

DETAILED DESCRIPTION OF THE INVENTION

In accordance with this invention, the protein conjugate of formula I is produced by condensing activated PEG where hydroxy has been replaced by an activated linker, with one or more of the free amino groups in the proteins. The activated PEG compounds used to produce the conjugate have the following formulae:

 II-A

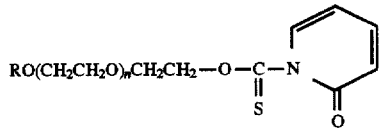 II-B

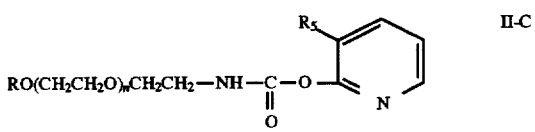 II-C

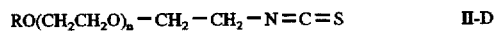 II-D

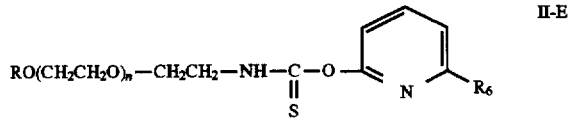 II-E

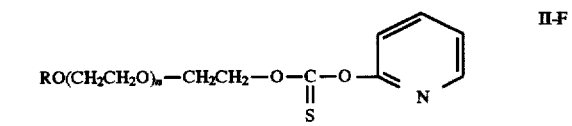 II-F

wherein R is as above, $R_4$ is lower alkyl or cycloalkyl, and $R_5$ and $R_6$ are lower alkyl or H.

In accordance with this invention, by using the activated PEG compound of formula II-A, II-B, II-C, II-D, II-E, or II-F to produce the conjugates, a linking bond between the free amino groups in the protein and the PEG is formed so that the resulting conjugate retains at least a portion of the biological activity of the protein while reducing its immunogenicity. In addition, the linkage groups formed in the conjugate of this invention through the use of any one of the activated polyethylene glycols of formulae II-A through II-F produces a protein conjugate which is not readily susceptible to in vivo hydrolytic cleavage and is not subject to many of the disadvantages present in the PEG protein conjugates of the prior art.

In accordance with this invention, $R_1$, $R_5$, and $R_6$ can be any lower alkyl, preferably methyl. The term lower alkyl designates lower alkyl groups containing from 1 through 6 carbon atoms, such as methyl, ethyl, n-propyl, isopropyl, etc. Generally the preferred alkyl group is a lower alkyl group containing from 1 to 4 carbon atoms with methyl being most preferable.

In accordance with this invention, m and n can be selected from any combination of numbers such that the resulting protein conjugate contains at least a portion of the biological activity of the polymer which forms the conjugate. It is apparent that the sum of n and m is inversely proportional to the amount of biological activity of the protein which is retained by the conjugate. The numerical value of n relates the number of ethylene glycol units in the polyethylene glycol which form the conjugate. The term m relates to the number of free amino groups contained by the protein which is reacted with the activated PEG. The higher the value of m and n, the higher the molecular weight of the conjugate.

When the compound of any one of formula II-A through II-F is reacted with the protein and the protein contains more than one free amino group, the conjugate may be produced as a mixture of various protein PEG conjugates. In cases where the protein contains two free amino groups, the activated PEG can react both with one of the free amino groups and with both of the free amino groups. In this situation the mixture contains one conjugate formed where two free amino groups are reacted with PEG and a second conjugate formed where only one free amino group is reacted with PEG. Since the various conjugates in this mixture have different molecular weights, these conjugates can be separated by conventional methods such as chromatography. To determine if m and n have been selected properly, the separated conjugates can be screened for biological activity by the same means used to screen the parent protein to determine if the conjugate still retains a portion of the biological activity of the protein used to form the conjugate. In this manner, the numbers m and n can be adjusted in any desired manner to provide the desired activity.

In accordance with the preferred embodiment of this invention m and n are any number so that molecular weight of the conjugate, excluding the weight of the protein, is between approximately 300 to approximately 30,000 daltons. In accordance with the preferred embodiment, m is 1. Where m is 1, this conjugate can be obtained even when there are two or more free amino groups. The activated PEG compound will react first with one of the free amino groups contained within the protein groups. By regulating the concentration of the reagents such as the protein, and reaction conditions, in accordance with standard methods of amine condensation, one can regulate the degree of pegylation of the free amino groups contained within the protein. In proteins containing one or more free amino groups, where one of the free amino groups is more reactive than the other amino groups, conditions may be selected so that the protein is reacted with the activated PEG compound to form the compound of formula I where m is 1. Other free amino groups contained within amino acids which form the protein may be subsequently reacted with the PEG by allowing the condensation reaction to proceed longer or by utilizing other stronger conditions. In accordance with a preferred embodiment where m is 1, n is any number so that the polyethylene glycol which forms the conjugate has a molecular weight of from 300 to 300,000 daltons.

Where $R_4$ is lower alkyl, $R_4$ can be any lower alkyl group containing from 1 to 6 carbon atoms such as defined above. When $R_5$ is cycloalkyl, $R_5$ is preferably a cycloalkyl group containing from 3 to 7 carbon atoms such as cyclopropyl, cyclopentyl, cyclobutyl, and cyclohexyl. The preferred cycloalkyl group is cyclohexyl.

The title compounds of each of the following Examples are named in accordance with IUPAC nomenclature. However, these compounds may also be named as follows:

Examples 1, 2, 3, and 4:
Alpha-[2-[[cyclohexylcarbonimidoyl)-amino]ethyl]-omega-methoxypoly (oxy-1,2-ethanediyl) is alternatively named alpha-[2-[[(cyclohexylamino)methylene]amino]ethyl] omega-methoxypoly-(oxy-1,2-ethanediyl).

Examples 1A, 1a, and 1d:
Alpha-(2-chloroethyl)-omega-methoxypoly(oxy 1,2-ethanediyl) is alternatively named alpha-methoxy-omega-(2-chloroethyl)poly(oxy-1,2-ethanediyl).

Examples 1B, 1b, and 1e:
Alpha-(2-azidoethyl)-omega-methoxypoly(oxy-1,2-ethanediyl) is alternatively named alpha-methoxy-omega-(2-azidoethyl)poly(oxy-1,2-ethanediyl).

Examples 1C, 1c, and 1f:
Alpha-(2-aminoethyl)-omega-methoxypoly(oxy-1,2-ethanediyl) is alternatively named alpha-methoxy-omega-(2-aminoethyl)poly(oxy-1,2-ethanediyl).

Examples 11, 11a, 11b, 12, 12A, and 13–17: Alpha-methyl-omega-[2-[[(2-pyridinyloxy)carbonyl]amino]ethoxy]poly (oxy-1,2-ethanediyl) is alternatively named alpha-[2-[[(2-pyridinyloxy)carbonyl]amino]ethyl]-omega-methoxypoly (oxy-1,2-ethanediyl).

Examples 18, 18a, 19, 19A, 20, 20A, 21, and 22:
Alpha-[(2-pyridinyloxy)carbonyl]omega-methoxypoly (oxy-1,2-ethanediyl) is alternatively named alpha-methyl-omega-[2-[[(2-pyridinyloxy)carbonyl]oxy]-ethoxy]poly-(oxy-1,2-ethanediyl).

Examples 23–27:
Alpha-[2-(isothiocyanato)ethyl]-omega-methoxypoly(oxy-1,2-ethanediyl) is alternatively named alpha-[methoxy-omega-[2-(isothiocyanato)ethyl]poly(oxy-1,2-ethanediyl).

Example 28:
Alpha-[(2-pyridinyloxy)thiocarbonyl]-omega-methoxypoly (oxy-1,2-ethanediyl) is alternatively named alpha-methyl-omega-[2-[[(2-pyridinyloxy)thiocarbonyl]oxy]ethoxy]-poly (oxy-1,2-ethanediyl).

To produce the protein conjugate wherein $R_2$ is —NH—, and $R_3$ is =N—$R_4$, (the compound of formula I-A) the following reaction scheme may be employed:

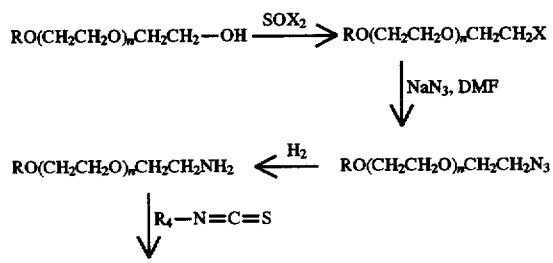

-continued

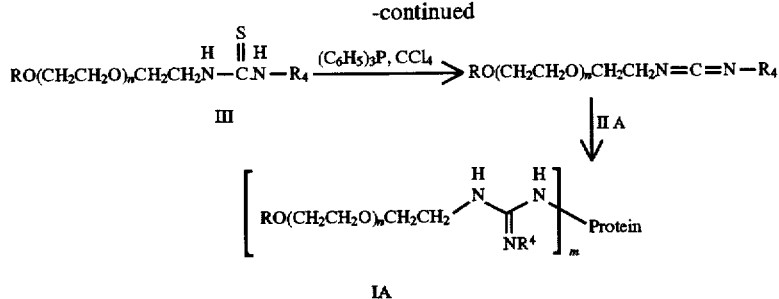

wherein R, R$_4$, n and m are as above,

In the reaction scheme, the hydroxyl group at the end of the PEG molecule is converted to a halogen group by conventional means such as by treatment with a thionyl halide. The resulting PEG halide is converted to an azide by conventional means such as by treatment with sodium azide. The PEG azide can then be converted to an amine by conventional means such as hydrogenation. The PEG-amine is then reacted with an alkyl or cycloalkyl isothiocyanate such as cyclohexylisothiocyanate to form the thiourea of formula III which is then desulfurized by conventional means to form the compound of formula II-A which contains the carbodiimide functional group. In converting the thiourea of formula III into the PEG carbodiimide of formula IIA, the preferred desulfurizing agent is triphenylphosphine.

The PEG carbodiimide of formula II-A can then be condensed with a protein under any conventional conditions for condensing carbodiimides with amines. Generally this reaction is carried out in a standard aqueous buffer solution having pH of between 7 and 9 to produce the conjugate of formula I-A. The resulting condensation reaction may produce a mixture of PEG protein conjugates of various molecular weights depending upon the number of free amino groups within the protein and the time of the reaction. The PEG protein conjugates may then be separated into their individual components by conventional methods such as high performance liquid chromatography or gel electrophoresis.

To produce the protein conjugate where R$_2$ is —O— and R$_3$ is =S, (the compound of formula IB) the following reaction scheme can be employed.

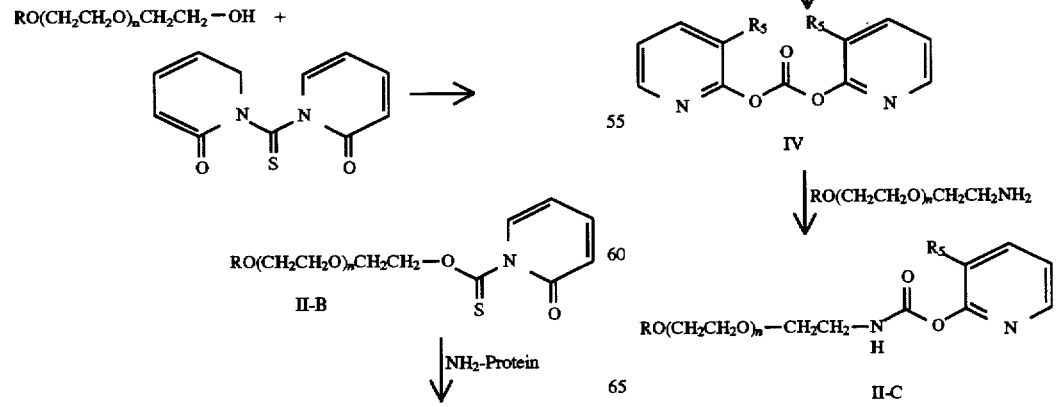

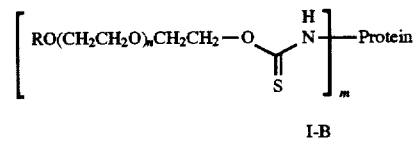

wherein R, m and n are as above,

In this reaction a PEG is refluxed with 1,1-carbonothioylbis-2(1H)-pyridinone in a high boiling hydrocarbon solvent to produce the compound of formula II-B. The compound of formula II-B can be condensed with one or more of the free amino groups of the protein to produce the conjugate of formula I-B in the same manner as described in connection with the condensation of the compound of formula II-A with a protein to prepare the conjugate mixture of formula I-A. Separation of this mixture can be carried out according to molecular weights of the products formed as described hereinbefore.

To produce the protein conjugate where R$_2$ is —NH— and R$_3$ is =O, (the compound of formula I-C) the following reaction scheme can be used:

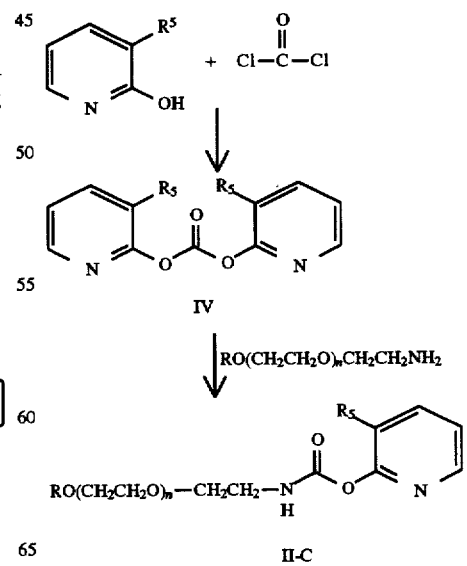

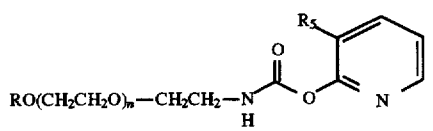

II-C

↓ NH₂-Protein

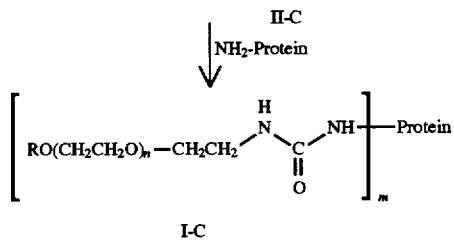

I-C wherein R, $R_5$, m and n are as above.

The compound of formula IV is produced by condensing phosgene with 2-hydroxypyridine (substituted if $R_5$=lower alkyl) using any conventional method for condensing an acid halide with an alcohol.

The condensation of a PEG amine with the compound of formula IV is effected by refluxing in a halogenated hydrocarbon solvent to produce the compound of formula II-C. The compound of formula II-C is condensed with the protein through one or more free amino groups on the protein to produce the compound of formula I-C. This reaction is carried out in the manner described for the condensation of the compound of formula II-A to produce the conjugate of formula I-A. Depending upon the number of free amino groups contained within the protein which react with the compound of formula II-C, the conjugate of formula I-C may be formed as a mixture of conjugates having different molecular weights. This conjugate mixture can be separated in the manner described hereinbefore.

To produce a protein conjugate of the present invention wherein $R_2$ is —NH— and $R_3$ is S, (the compound of formula I-D) the following reaction scheme can be used.

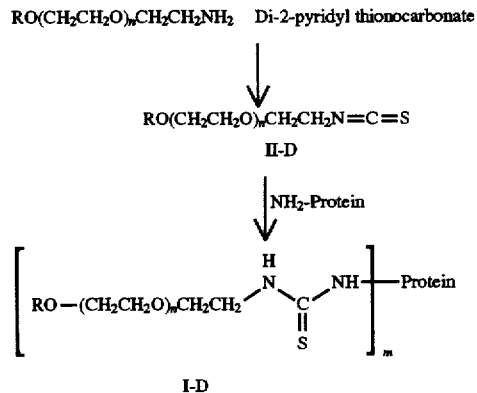

wherein R, m and n are as above.

In this reaction scheme, PEG amine is reacted with di-2-pyridylthionocarbonate to produce the compound of formula II-D. In this procedure any conventional method of condensing an amine with a thiocarbonate to produce an isothiocyanate can be used. The compound of formula II-D is reacted with the protein to form the conjugate of formula I-D in the manner described for the conversion of the compound of formula II-A to the compound of formula I-A. Depending upon the amount of free amino groups contained by the protein, condensation of the compound of formula II-D with the protein produces a mixture of conjugates which can be separated into their individual components in the manner hereinbefore described for the separation of the conjugate of formula I.

Alternatively, the compound of formula I-D can be produced using the following reaction scheme:

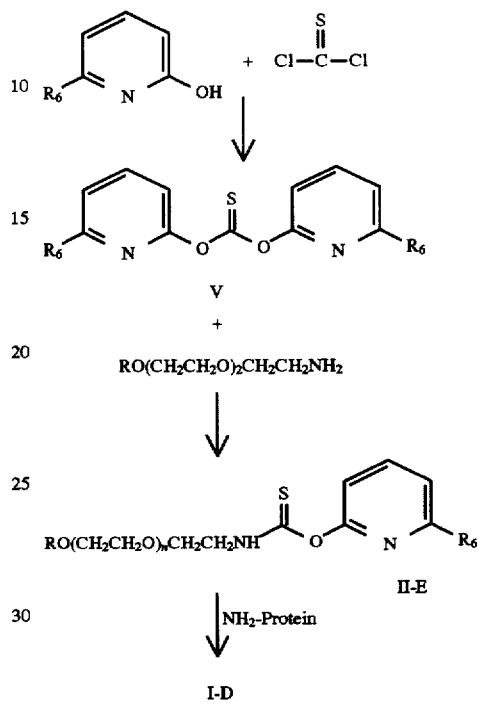

The compound of formula V is produced by condensing thiophosgene with 2-hydroxypyridine (substituted where R6 is lower alkyl), using any conventional method for condensing an acid halide with an alcohol. V is then reacted with a PEG-amine in the manner described for producing the compound of II-C. The resulting compound is II-E. The compound of formula II-E is condensed with one or more free amino groups on a protein to produce the conjugate of formula I-D. This reaction is carried out in the manner described for the formation of conjugate I-A.

The protein conjugate of the present invention where $R_2$ is —O— and $R_3$ is =S, (the compound of formula I-E) is produced by the following reaction scheme:

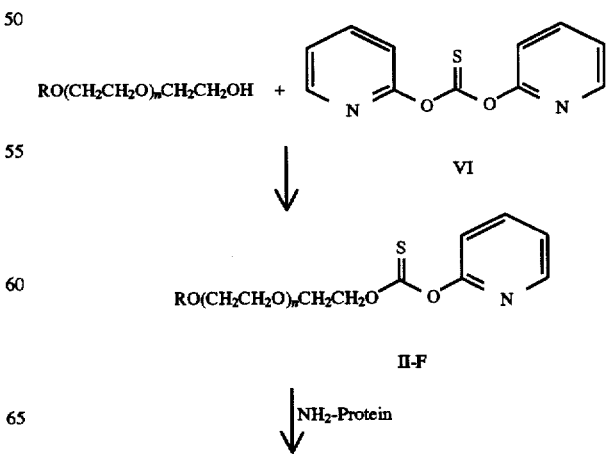

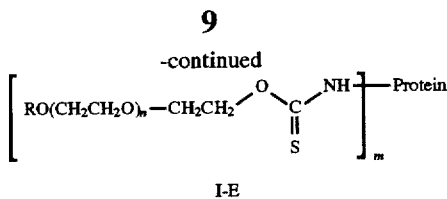

I-E

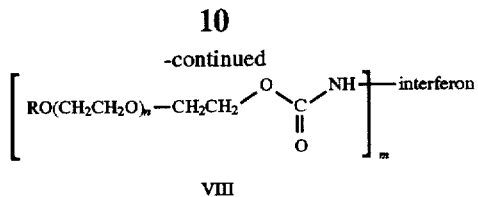

VIII wherein R, m and n are as above.

In accordance with this scheme, PEG is reacted with the thiocarbonate of formula VI in an organic solvent to form the PEG thiocarbonate of formula II-F. Any conventional method of condensing a thiocarbonate with a hydroxy group can be used in carrying out this reaction.

The compound of formula II-F is converted to the conjugate of formula I-E by condensing the compound of formula II-F with at least one free amino group of the protein. This reaction is carried out in the manner described for the conversion of compound of formula II-A to the conjugate of formula I-A. The product that is produced by this reaction can be a mixture of conjugates of different molecular weights depending upon the amount of free amino groups in the protein used. These conjugates can be separated by molecular weight in accordance with the procedure hereinbefore described.

The interleukin-1 receptor antagonist (IL-1ra) herein may be obtained from tissue cultures or by recombinant techniques. One method of obtaining IL-1ra is to treat U937 human myelomonocytic cells (ATCC CRL 1594) with the differentiating agent phorbol myristate acetate (PMA) and then stimulate them with Granulocyte Macrophage-Colony Stimulating Factor (obtainable from Amgen), and isolating and purifying the IL-1ra from the culture supernatant liquid as described by Carter et al. Nature 344 633–637 (1990).

Recombinant IL-1ra refers to IL-1ra having comparable biological activity to native IL-1ra but prepared by recombinant techniques as described by Carter et al. supra or by Eisenberg et al. Nature 343 341–346 (1990).

In accordance with this invention, it has been found that the protein-conjugates of this invention have the same utility as the protein used to form the conjugate. Therefore, these conjugates are therapeutically active in the same manner as the protein from which they are formed and can be used in the same manner as this protein without producing the immune response connected with the administration of proteins to subjects.

In accordance with another embodiment of this invention, an interferon composition can be produced by the following reaction scheme:

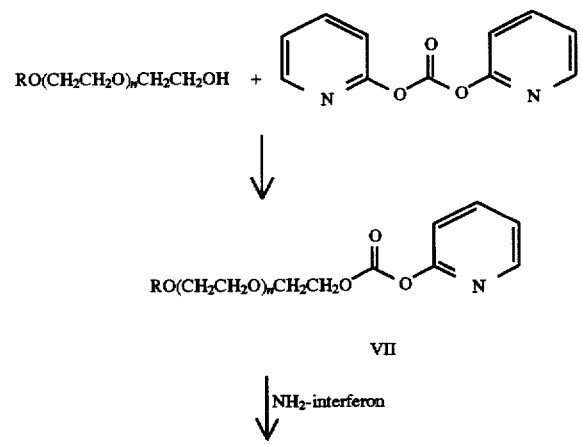

wherein R, m, and n are as above.

In the above reaction scheme, di-2-pyridyl carbonate is reacted with PEG-alcohol to produce the compound of formula VII. This reaction is carried out using conventional conditions for condensing an alcohol with a carbonate. The compound of formula VII is converted to the compound of formula VIII by condensing the former compound with one or more free amino groups of the protein interferon. This reaction is carried out as described for the conversion of the compound of formula II-A to the compound of formula I-A. The reaction mixture thus produced can contain a mixture of the conjugates of formula VIII depending on the number of free amino groups contained by the protein. This mixture constitutes a mixture of various conjugates of different molecular weights. The various conjugates can be separated from the mixture as described hereinbefore.

Interferon includes all types of interferon, such as α, β, and δ interferon, and any subtypes of any types. Interferon may be obtained from tissues or tissue cultures, or may be produced using recombinant techniques. Methods for generating and isolating natural or recombinant interferon are well known in the art.

EXAMPLE 1

Preparation of alpha-[2-[[(Cyclohexylcarbonimidoyl)-amino]ethyl]-omega-methoxypoly(oxy-1,2-ethanediyl) SRU 111.7.

A. Preparation of alpha-(2-Chloroethyl)-omega-methoxypoly (oxy-1,2-ethanediyl) SRU 111.7 (As used herein SRU designates the number of self-repeating units present in the PEG polymer).

From a slurry of 50 g MPEG (methoxypolyethylene glycol, molecular weight-5000) in 700 ml of toluene was distilled 200 ml of the solvent. To the refluxing solution was added dropwise 0.8 ml of dry pyridine and 2.2 ml of thionyl chloride. After refluxing for four hours the reaction was allowed to stir overnight. The solvent was then removed under reduced pressure and 500 ml of $CH_2Cl_2$ added to the residue. The resultant solution was then dried with anhydrous $K_2CO_3$ and passed through 50 g of basic alumina (Wolem Super I). Most of the $CH_2Cl_2$ was then removed under reduced pressure and one liter of diethyl ether added to the resultant syrup. The ether was removed by distillation and additional diethyl ether added to cause precipitation. The mixture was stirred at room temperature for two hours and then filtered to give 45 g of alpha-(2-chloroethyl)-omega-methoxypoly (oxy-1,2-ethanediyl) SRU 111.7

Anal. Calcd for $C_3H_7ClO(CH_2CH_2O)_{111.7}$ C, 53.97; H, 9.12; Cl, 0.71. Found: C, 54.21 H, 8.70; Cl, 0.71

B. Preparation of alpha-(2-Azidoethyl)-omega-methoxypoly (oxy-1,2-ethanediyl) SRU 111.7

A mixture of 20 g of sodium azide and 50 g of alpha-(2-chloroethyl)-omega-methoxypoly (oxy-1,2-ethanediyl) SRU 111.7 was heated at 120°–125° C. in 375 ml of dry DMF. After 7 hours the solvent was removed under high vacuum. The residue was dissolved in 500 ml of $CH_2Cl_2$ and filtered through diatomaceous earth. Most of the $CH_2Cl_2$ was then boiled off and diethyl ether added to cause precipitation. The mixture was stirred overnight and then fil-

11 tered. The residue was then dissolved in a minimum of glyme at 50° C., the solution cooled, and the precipitated product filtered to give alpha-(2-azidoethyl)-omega-methoxypoly (oxy-1,2-ethanediyl) SRU 111.7

Anal. Calcd for $C_3H_3N_3O(CH_2CH_2O)_{111.7}$: C, 53.77; H, 9.09; N, 0.84. Found: C, 53.61; H, 9.08; N, 0.89.

C. Preparation of alpha-(2-Aminoethyl)-omega-methoxypoly (oxy-1,2-ethanediyl) SRU 111.7

To a mixture of 25 g of alpha-(2-azidoethyl)-omega-methoxypoly (oxy-1,2-ethanediyl) SRU 111.7 in 250 ml of dry glyme was added 3.5 g of 10% Pd/C. The mixture was then placed under an atmosphere of 50 p.s.i. of $H_2$ and shaken at 50° C. for 18 hours. The mixture was then filtered, the solids washed with $CH_2Cl_2$ and the combined organic solutions placed under reduced pressure to remove the solvent. The residue was then dissolved in 100 ml of warm glyme, and the product allowed to precipitate from the cooled solution. The precipitate was filtered and dried by warming under reduced pressure to give 23 g of alpha-(2-aminoethyl)-omega-methoxypoly (oxy-1,2-ethanediyl) SRU 111.7

Anal. Calcd for $C_3H_9NO(CH_2CH_2O)_{111.7}$: C, 54.43; H, 9.20; N, 0.28. Found: C, 54.43; H, 9.18; N, 0.36.

Alternatively a solution of 40 g of alpha-(2-azidoethyl)-omega-methoxypoly (oxy-1,2-ethanediyl) SRU 111.7 and 6.7 g (25.6 mmol) of triphenylphosphine dissolved in 200 ml of dry $CH_2Cl_2$ was stirred overnight under an atmosphere of argon. Water (2 ml) was added and the mixture stirred an additional 12 hours. Most of the methylene chloride was removed under vacuum and 400 ml of diethyl ether added. The precipitate was filtered, washed with ether and dissolved in 300 ml of warm (50° C.) glyme. The solution was allowed to stand at room temperature overnight and the resulting precipitate filtered, washed with 2×100 ml of glyme, 2×100 ml of diethyl ether and dried in a vacuum oven under a stream of $N_2$ to give 35 g of alpha-(2-aminoethyl)-omega-methoxypoly (oxy-1,2-ethanediyl) SRU 111.7

D. Preparation of alpha-[2-[[(Cyclohexylamino)thiocarbonyl]-amino]ethyl]-omega-methoxypoly(oxy-1,2-ethanediyl) SRU 111.7

To a solution of 4 g of alpha-(2-aminoethyl)-omega-methoxypoly (oxy-1,2-ethanediyl) SRU 111.7 in 60 ml of dry glyme at 40° C. was added 0.1 ml of cyclohexyl isothiocyanate. The solution was allowed to stir at 40° C. for 18 hours. The mixture was then filtered and the solvent removed under high vacuum. The residue was then dissolved in 100 ml of warm glyme, the solution cooled and the resulting precipitate filtered and dried under high vacuum to give 3.5 g of alpha-[2-[[(cyclohexylamino)thiocarbonyl]-amino]ethyl]-omega-methoxypoly(oxy-1,2-ethanediyl) SRU 111.7

Anal. Calcd for $C_{10}H_{20}N_2OS(CH_2CH_2O)_{111.7}$: C, 54.25; H, 9.13; N, 0.54; S, 0.62; Found: C, 54.39; H, 8.87; N, 0.55; S, 0.59.

E. Preparation of alpha-[2-[[(Cyclohexylcarbonimidoyl)amino]-ethyl]-omega-methoxypoly(oxy-1,2-ethanediyl) SRU 111.7.

A solution of 1 g of alpha-[2-[[(Cyclohexylamino)thiocarbonyl]amino]ethyl]-omega-methoxypoly(oxy-1,2-ethanediyl) SRU 111.7, 120 mg of triphenylphosphine, 90 µl of $CCl_4$ and 84 µl of triethylamine in 5 ml of dry $CH_2Cl_2$ was refluxed for 72 hr. The solvent was then removed under reduced pressure and the residue dissolved in a minimum of dry glyme. After cooling, the product precipitated and was filtered and dried under vacuum to give alpha-[2-[[(cyclohexylcarbonimidoyl)amino]ethyl]-omega-methoxypoly-(oxy-1,2-ethanediyl) SRU 111.7.

12

Anal. Calcd for $C_{10}H_{18}N_2O(CH_2CH_2O)_{111.7}$: C, 54.61; H, 9.15; N, 0.55. Found: C, 54.95; H, 9.27; N, 0.50

Example 1a

Preparation of alpha-(2-Chloroethyl)-omega-methoxypoly(oxy-1,2-ethanediyl) SRU 225

By the procedure described in Example 1A, MPEG molecular weight 10,000 was converted to alpha-(2-chloroethyl)-omega-methoxypoly (oxy-1,2-ethanediyl) SRU 225.

Anal. Calcd for $C_3H_7ClO(CH_2CH_2O)_{225}$: C, 54.37; H, 9.14; Cl, 0.35. Found: C, 54.30; H, 9.15; Cl, 0.41.

Example 1b

Preparation of alpha-(2-Azidoethyl)-omega-methoxypoly(oxy-1,2-ethanediyl) SRU 225

By the procedure described in Example 1B, alpha-(2-chloroethyl)-omega-methoxypoly(oxy-1,2-ethanediyl) SRU 225 was converted to alpha-(2-azidoethyl)-omega-methoxypoly (oxy-1,2-ethanediyl) SRU 225.

Anal. Calcd for $C_3H_7N_3O(CH_2CH_2O)_{225}$: C, 54.34; H, 9.13; N, 0.42. Found: C, 54.32; H, 9.28; N, 0.50.

Example 1c

Preparation of alpha-(2-Aminoethyl)-omega-methoxypoly(oxy-1,2-ethanediyl) SRU 225

By the procedure described in Example 1C, alpha-(2-azidoethyl)-omega-methoxypoly(oxy-1,2-ethanediyl) SRU 225 was converted to alpha-(2-aminoethyl)-omega-methoxypoly (oxy-1,2-ethanediyl) SRU 225.

Anal. Calcd for $C_3H_9NO(CH_2CH_2O)_{225}$: C, 54.48; H, 9.17; N, 0.14. Found: C, 54.80; H, 9.21; N, 0.12.

Example 1d

Preparation of alpha-(2-Chloroethyl)-omega-methoxypoly (oxy-1,2-ethanediyl) SRU 28.3

To a solution of freshly distilled oxalyl chloride (0.5 ml) in 40 ml of dry $CH_2Cl_2$ at 0° C. was added dropwise 0.5 ml of dry DMF in 10 ml of $CH_2Cl_2$. The resulting solution was warmed to room temperature, stirred for 15 min and then again cooled to 0° C. MPEG molecular weight 1325, (5.6 gr) was then added, and the resulting solution refluxed for 5 hr. The mixture was then poured into water and the mixture extracted with $CH_2Cl_2$. The $CH_2Cl_2$ solution was dried ($MgSO_4$) and the solvent removed under reduced pressure to give 1.7 g of alpha-(2-chloroethyl)-omega-methoxypoly (oxy-1,2-ethanediyl) SRU 28.3 as a white powder.

Anal. Calcd for $C_3H_7ClO(CH_2CH_2O)_{28.3}$: C, 53.38; H, 9.03; Cl, 2.64. Found: C, 53.48; H, 9.10; Cl, 2.41.

Example 1e

Preparation of alpha-(2-Azidoethyl)-omega-methoxypoly (oxy-1,2-ethanediyl) SRU 28.3

By the procedure described in Example 1B, alpha-(2-chloroethyl)-omega-methoxypoly(oxy-1,2-ethanediyl) SRU 28.3 was converted to alpha-(2-azidoethyl)-omega-methoxypoly (oxy-1,2-ethanediyl) SRU 28.3.

Anal. Calcd for $C_3H_7N_3O(CH_2CH_2O)_{28.3}$: C, 53.12; H, 8.99; N, 3.11. Found: C, 53.21; H, 9.07; N, 2.98.

Example 1f

Preparation of alpha-(2-Aminoethyl)-omega-methoxypoly (oxy-1,2-ethanediyl) SRU 28.3

By the procedure described in Example 1C, alpha-(2-azidoethyl)-omega-methoxypoly(oxy-1,2-ethanediyl) SRU 28.3 was converted to alpha-(2-aminoethyl)-omega-methoxypoly (oxy-1,2-ethanediyl) SRU 28.3.

Anal. Calcd for $C_3H_9NO(CH_2CH_2O)_{28.3}$: C, 54.47; H, 9.17; N, 0.14. Found: C, 54.44; H, 9.19; N, 0.15.

EXAMPLE 2

Preparation of Recombinant Interferon-alpha (IFN-alpha) Conjugated to PEG by means of the reagent alpha-[2-[[(Cyclohexylcarbonimidoyl)amino]-ethyl]-omega-methoxypoly(oxy-1,2-ethanediyl) SRU 111.7.

alpha-[2-[[(Cyclhexylcarbonimidoyl)amino]ethyl]-omega-methoxypoly(oxy-1,2-ethanediyl) SRU 111.7 prepared according to Example 1 was added to 1 mg of homogenous IFN-alpha in 200 ul of buffer (0.1M sodium borate, pH 9.0) in a molar ratio of 10 moles of reagent per one mole IFN-alpha. The solutions were thoroughly mixed and the pegylation reaction allowed to proceed at room temperature for 60 minutes.

The amount of derivatization (or pegylation) of IFN-alpha was estimated by SDS-polyacrylamide gel electrophoresis (SDS-PAGE) (TABLE I). Proteins were visualized by Coomassie Blue staining. Analysis of the products from the 60 min. reaction reveals new higher molecular weight protein species corresponding to PEG-conjugated IFN-alpha. IFN-alpha has an apparent molecular weight of 15 kD by SDS-PAGE. Unmodified IFN-alpha whose apparent molecular weight remains unchanged is therefore not conjugated with PEG. The PEG-modified IFN-alpha product has an apparent molecular weight of 28 kD.

TABLE I

Modification of IFN-alpha with the reagent described in Example 1

| Apparent Molecular Weight of IFN Protein (kD) | % of Total Protein from Reaction |
| --- | --- |
| 15 (unmodified) | 80 |
| 28 | 20 |

EXAMPLE 3

Preparation of Recombinant Interleukin-2 (rIL-2) conjugated to PEG by means of the reagent alpha-[2-[[(Cyclohexylamino]amino]ethyl]-omega-methyoxypoly(oxy-1,2-ethanediyl) SRU 111.7.

Alpha-[2-[[(cyclohexylamino]amino]ethyl]-omega-methoxypoly(oxy-1,2-ethanediyl) SRU 111.7 prepared according to Example 1 was added to 2 mg of rIL-2 in 200 ul of buffer (0.1M sodium borate, pH 9.0) in a molar ratio of 10 moles of reagent per one mole rIL-2. The solutions were thoroughly mixed and the pegylation reaction was allowed to proceed at room temperature for 60 minutes.

The amount of derivatization (or pegylation) of the protein was estimated by SDS-PAGE (Table II). Proteins were visualized by Coomassie Blue staining. Analysis of the products from the 60 min. reaction reveals new higher molecular weight protein species. corresponding to PEG-conjugated rIL-2. rIL-2 has an apparent molecular weight of 15 kD by SDS-PAGE. Unmodified rIL-2 is the protein separated from the reaction mixture whose molecular weight remains unchanged and is therefore not conjugated with PEG. The predominant PEG-modified rIL-2 product has an apparent molecular 28 kD.

TABLE II

Modification of rIL-2 with the reagent described in Example 1

| Apparent Molecular Weight of rIL-2 Protein (kD) | % of Total Protein from Reaction |
| --- | --- |
| 15 (unmodified) | 20 |
| 28 | 50 |
| 33 | 20 |
| 43 | 10 |

Pegylated rIL-2 was purified from the reaction mixture as describe by Katre et al. [Proc. Nat. Acad. Sci., USA, 84:1483, (1987)] using hydrophic exchange chromatography (Bio-Rad; Biogel-phenyl 5-PW). A linear gradient with decreasing salt from 1.53 to 0.0M $(NH_4)_2SO_4$ in 50 mM sodium phosphate pH 7.0 in 30 minutes was used to PEG-modified and unmodified rIL-2. Aliquots of the fractions were evaluated by SDS-PAGE and pooled fractions were assayed to determine its specific activity in a CTLL cell proliferation assay by the method described by Gillis et al. [J. Immunology 120:2027, (1978)]. Protein concentrations were determined spectrophotometrically at 280 nm using an extinction coefficient of 0.667 for rIL-2. The specific activity of the rIL-2 isolated proteins is expressed as units/mg protein and the results are summarized in Table III. It is apparent that specific activity of rIL-2 is not significantly altered by conjugation with PEG.

TABLE III

Bioactivity of rIL-2 conjugated to PEG with the reagent described in Example 1

| Apparent Molecular Weight of rIL-2 Protein (kD) | Specific Activity (units/mg) |
| --- | --- |
| 15 (unmodified IL2) | $2.0 \times 10^7$ |
| 28 | $2.4 \times 10^7$ |

EXAMPLE 4

Preparation of Recombinant Interleukin 1-alpha (rIL-1 alpha) Conjugated to PEG by means of the reagent alpha-2-[[(Cyclohexylamino]amino]ethyl] omega-methoxypoly(oxy-1,2-ethanediyl) SRU 111.7.

The reagent described in Example 1 was added to 2.0 mg of homogenous rIL-1 alpha in 1.0 ml 0.1M sodium borate, pH 9.0 in a molar ratio of 10 moles of reagent per one mole rIL-1 alpha. The solution was thoroughly mixed and the pegylation reaction was allowed to proceed at room temperature for 60 minutes.

The amount of derivatization (or pegylation) of the protein was estimated by SDS-PAGE (Table IV). The proteins were visualized by Coomassie Blue staining. Analysis of the products from the 60 minute reaction reveals new higher molecular weight protein species corresponding to PEG conjugated rIL-1 alpha protein. rIL-1 alpha has an apparent molecular weight of 17 kD by SDS-PAGE. Unmodified rIL-1 alpha is protein from the reaction mixture whose apparent molecular weight remains unchanged and is therefore not conjugated with PEG. The PEG-modified rIL-1 alpha product has an apparent molecular weight of 30 kD.

TABLE IV

Modification of rIL-1 alpha with the reagent described in Example 1

| Apparent Molecular Weight of rIL-1 alpha Protein (kD) | % of Total Protein from Reaction |
|---|---|
| 17 (unmodified) | 85 |
| 30 | 15 |

EXAMPLE 5

Preparation of alpha-[(1,2-Dihydro-2-oxo-1-pyridinyl)-thiocarbonyl]-omega-methoxypoly(oxy-1, 2-ethanediyl) SRU 111.7

From a solution of 1 g (0.2 mmol) MPEG (methoxypolyethylene glycol) molecular weight of 5000, in 15 ml of dry toluene was distilled 5 ml of solvent. The resulting solution was cooled and 46.5 mg (0.2 mmol) of 1,1-carbonothioylbis-2(1H)-pyridinone was added. The mixture was then refluxed under an atmosphere of argon for 4 hours. The solvent was then removed under vacuum and the residue dissolved in 5 ml of dry glyme and let stand overnight. The resulting precipitate was then filtered and washed with 2×5 ml of dry glyme and 5 ml of diethyl ether. The product was then dried in a vacuum oven under a slow stream of nitrogen to give 0.96 g of alpha-[(1,2-dihydro-2-oxo-1-pyridinyl)thiocarbonyl]-omega-methoxypoly(oxy-1, 2-ethanediyl) SRU 111.7.

Anal. Calcd for $C_9H_{11}NO_3S(CH_2CH_2O)_{111.7}$: C, 54.37; H, 8.99; N, 0.27; S, 0.62; Found: C, 54.03; H, 8.98; N, 0.18; S, 0.59.

Example 5a

Preparation of alpha-[(1,2-Dihydro-2-oxo-1-pyridinyl)-thiocarbonyl]omega-methoxypoly(oxy-1, 2-ethanediyl) SRU 225

By the procedure described in Example 5, MPEG (methoxypoly-ethylene glycol) molecular weight 10,000 was converted to alpha-[(1,2-dihydro-2-oxo-1-pyridinyl) thiocarbonyl]-omega-methoxy-poly(oxy-1,2-ethanediyl) SRU 225.

Anal. Calcd for $C_9H_{11}NO_3S(CH_2CH_2O)_{225}$: C, 54.54; H, 9.08; N, 0.14; S, 0.32. Found: C, 54.38; H, 9.16; N, 0.15; S, 0.31.

EXAMPLE 6

Preparation of Interleukin 1 receptor antagonist (IL-1ra) conjugated to PEG by means of the reagent alpha-[(1,2-Dihydro-2-oxo-1-pyridinyl)thiocarbonyl] omega-methoxy-poly-(oxy-1,2-ethanediyl) SRU 111.7.

Alpha-[(1,2-dihydro-2-oxo-1-pyridinyl)thiocarbonyl]-omega-methoxy-poly(oxy-1,2-ethanediyl) SRU 111.7 prepared according to Example 5 was added to 10 mg of homogenous IL-1ra in 1.0 ml of buffer (0.1M sodium borate, pH 9.0) in a molar ratio of 5 moles of reagent per one mole of IL-1ra. The solution was thoroughly mixed and the pegylation reaction was allowed to proceed at room temperature for 60 minutes.

The amount of derivatization (or pegylation) of the protein was estimated by SDS-PAGE (Table V). Proteins were visualized by Coomassie Blue staining. Analysis of the products from the 60 minute reaction reveals new higher molecular weight protein species corresponding to PEG-conjugated IL-1ra protein. IL-1ra has an apparent molecular weight of 19 kD by SDS-PAGE. Unmodified IL-1ra is the protein from the reaction mixture whose apparent molecular weight remains unchanged and is therefore not conjugated with PEG.

The predominant PEG-modified IL-1ra proteins have apparent molecular weights of 26 and 33 kD.

TABLE V

Modification of IL-1ra with the reagent described in Example 5

| Apparent Molecular Weight of Il-1ra Protein (kD) | % of Total Protein from Reaction |
|---|---|
| 19 (unmodified) | 36 |
| 26 | 33 |
| 33 | 21 |
| >33 | 10 |

Pegylated IL-1ra was purified from the reaction mixture using hydrophobic exchange chromatography (Bio-Rad; HRLC MP7 HIC). A linear gradient with decreasing salt concentrations from 0.43 to 0.0M $(NH_4)_2SO_4$ in 50 mM sodium phosphate pH 7.0 in 20 minutes was used to separate pegylated IL-1ra and unmodified IL-1ra. Aliquots of fractions were evaluated by SDS-PAGE and pooled fractions were assayed in an IL-1 radioreceptor competition binding assay. [Kilian et al. J. Immunol., 136, 4509, (1986)]. Briefly, IL-1ra and PEG-IL-1ra were incubated at varying concentrations with EL-4 membranes for 30 min at 37° C. The [$^{125}$I]IL-1 alpha was then added and the incubation continued for 30 min. The assay was terminated by vacuum filtration and the collection of cell bound [$^{125}$I]IL-1 on filter plates. The concentration of IL-1ra or PEG-IL-1ra that inhibits binding of [$^{125}$I]IL-1 by 50% ($IC_{50}$) was determined graphically. The results are shown in TABLE VI. The $IC_{50}$ of IL-1ra in this assay is 1–2.0 ng/ml. The pegylated IL-1ra mixture retained its ability to bind to the IL-1 receptor on EL-4 membranes within a factor 2 to 3 fold relative to the unmodified II-1ra.

TABLE VI

Inhibition of [$^{125}$I] IL-1 Binding by of IL-1ra Conjugated with the reagent described in Example 5

| Apparent Molecular Weight of IL-1ra Protein (kD) | $IC_{50}$ (ng/ml) |
|---|---|
| 19K (unmodified) | 2.0 |
| 26K, 33K (mixture) | 5.0 |

The pharmacodynamics of IL-1ra protein was evaluated in vivo by the ability of the IL-1ra to inhibit rIL-1alpha induction of interleukin-6. Serum from mice treated with rIL-1alpha contain high levels of IL-6. [McIntosh et al., Immunol. 143: 162, (1989)]. The administration of unmodified IL-1ra together with IL-1alpha (0 hr time point) inhibits the induction of IL-6. This test system was used to compare the pharmacodynamic properties of unmodified and PEG IL-1ra. Groups of three female C57Bl/6 mice were injected subcutaneously with 200 ug of unmodified IL-1ra or PEG-IL-1ra 48 hr, 24 hr, or 6 hr before or simultaneously (0 hr) with 0.2 ug rIL-1 alpha. Three hours later, serum samples were collected. IL-6 levels (units) were determined using a modification of an IL-6 assay that has been previously described [Van Snick et al., Proc. Natl. Acad. Sci. USA 83:9679, (1986)]. In the IL-6 assay, B9 hybridoma cells were treated with two fold serial dilutions of the test sera in 96-well microtiter plates. Following a 3 day incubation at 37° C. in a humidified atmosphere comprised of 5% $CO_2$ and 95% air, the wells were pulsed with 0.5 uCi of tritiated thymidine and incubated for an additional 18 hr. The cells were then harvested onto glass fiber filters and the level of tritiated thymidine incorporation was determined by scintillation counting. IL-6 activity is expressed as U/ml. IL-6 units are defined as the inverse of the serum dilution which produces half-maximal tritiated thymidine incorporation compared to a reference standard.

The pharmacodynamic data are summarized in Table D1. Mice treated only with IL-1 exhibited 28852 U/ml IL-6. Both unmodified and modified IL-1ra inhibited IL-6 induction at 0 hr. However, the pegylated IL-1ra demonstrated a prolonged IL-6-inhibitory effect as compared to unmodified IL-1ra at 8 and 24 hours after administration.

TABLE D1

Pharmacodynamic Profile of IL-1ra Conjugated with the reagent described in Example 5

| Time (hr.) Prior to | IL-6 (Units/ml) | |
|---|---|---|
| IL-1 Administration | 19 kD | 26 kD |
| 0 | 772 | 705 |
| 6 | 8361 | 1587 |
| 24 | 22525 | 9844 |
| 48 | 18485 | 21119 |
| 72 | 13220 | 21470 |

Example 6A

Preparation of Interleukin 1 receptor antagonist (IL-1ra) conjugated to PEG by means of the reagent alpha-[(1,2Dihydro-2-oxo-1-pyridinyl)thiocarbonyl]-omega-methoxypoly-(oxy-1,2-ethanediyl) SRU 225.

IL-1ra was conjugated and purified according to the procedure illustrated in Example 6 using the reagent described in Example 5a.

The predominant PEG-modified IL-1ra proteins have apparent molecular weights of 33 kD and 48 kD. The 33 kD and 48 kD protein accounted for 46 and 27% of the total protein in the reaction mixture, respectively.

The ability of these proteins to inhibit IL-1 binding, as described in Example 6, is summarized in Table VII. The 33 kD PEG modified protein retains the ability to inhibit IL-1 binding within 6-fold IL1ra and more extensive modification of the protein with PEG as observed with this 48 kD protein results in a substantial loss in its binding to the IL-1 receptor.

TABLE VII

Inhibition of [$^{125}$I] IL-1 Binding by IL-1ra Proteins Conjugated with the reagent described in Example 5a

| Apparent Molecular Weight of IL-1ra Protein (kD) | $IC_{50}$ (ng/ml) |
|---|---|
| 19 (unmodified) | 1.6 |
| 33 | 9.0 |
| 48 | 50.0 |

To determine the pharmacokinetic profile of PEG-IL-1ra species, C57BF/6 mice were administered 100 ug of modified or pegylated IL-1ra species subcutaneously. Serum samples were collected after 1, 2, 3, 4 and 6 hours from mice that received unmodified IL-1ra and after 2, 4, 8, 10, and 24 hours from mice that received PEG-IL-1ra. The serum levels were determined in the EL4 membrane binding assay described in Example 6. The data are summarized in Table D2. The PEG-IL-1ra was detectable in serum samples at higher concentrations and for prololoned time compared to IL-1ra demonstrating a prolonged serum time course.

TABLE D2

Pharmacokinetic Profile of IL-1ra pegylated as in Example 6a

| | Serum Concentration of IL-1ra | |
|---|---|---|
| Time (hr.) After Administration | 19 kD | 33 kD |
| 1 | 400 | |
| 2 | 130 | 2500 |
| | 40 | |
| 4 | 15 | 800 |
| 6 | 16 | |
| 8 | | 300 |
| 10 | | 250 |
| 24 | | 15 |

EXAMPLE 7

Preparation of rIL-1 alpha conjugated to PEG by means of the reagent alpha-[(1,2-dihydro-2-oxo-1-pyridinyl)-thiocarbonyl]omega-methoxy-poly(oxy-1,2-ethanediyl) SRU 111.7.

Recombinant IL-1 alpha was pegylated with the reagent described in Example 5 by the method as described in Example 4. Three predominant molecular weight species from the reaction mixture were identified by SDS-PAGE with apparent molecular weights corresponding to 17 (unmodified), 26, and 33 kD. The latter two pegylated proteins accounted for 25 and 55% of the total protein, respectively.

Pegylated rIL-1 alpha was purified from the reaction mixture after 60 minutes using hydrophobic exchange chromatography (Bio-Rad; HRLC MP7 HIC). A linear gradient with decreasing salt concentration from 0.43 to 0.0M $(NH_4)_2SO_4$ in 50 mM sodium phosphate pH 7.0 in 20 minutes was used to separate pegylated rIL-1 alpha and unmodified rIL-1 alpha. Aliquots of fractions were evaluated by SDS-PAGE and pooled fractions were assayed for specific activity in a D10 cell proliferation assays by the method described by Kaye et al. [J. Exp. Med. 158:836, (1983)]. Protein concentrations were determined spectrophotometrically at 280 nM using an extinction coefficient of 1.0 for rIL-1 alpha. The specific activity of the rIL-1 alpha is approximately $1.0 \times 10^8$ units/mg. The specific activity results are summarized in Table VIII. The 26 kD pegylated IL-1 alpha conjugate retains bioactivity within 2-3 fold of relative to IL-1 alpha. Further modification resulting in a 33 kD protein results in substantial loss of bioactivity.

TABLE VIII

Bioactivity of rIL-1alpha Conjugated with the reagent described in Example 5

| Apparent Molecular Weight of rIL-1 alpha Protein (kD) | Specific Activity (units/mg) |
|---|---|
| 17 (unmodified) | $4.6 \times 10^7$ |
| 26 | $1.9 \times 10^7$ |
| 33 | $4.5 \times 10^6$ |

EXAMPLE 8

Preparation of IFN-alpha conjugated to PEG by means of alpha-[(1,2-Dihydro-2-oxo-1-pyridinyl)thiocarbonyl]-omega-methoxypoly(oxy-1,2-ethanediyl) SRU 111.7 alpha-[(1,2-Dihydro-2-oxo-1-pyridinyl)thiocarbonyl]-omega-methoxypoly(oxy-1,2-ethanediyl) SRU 111.7 prepared according to Example 5, was added to 1 mg of purified IFN-alpha in 100 ul of buffer (0.1M sodium borate, pH 9.0) in a molar ratio of 8 moles of the PEG reagent per one mole IFN-alpha. The solutions were thoroughly mixed and the pegylation reaction was allowed to proceed at room temperature for 60 minutes.

The predominant molecular weight species from the reaction mixture were identified by SDS-PAGE with apparent molecular weights of 15 (unmodified), and 28 kD. The 28 kD pegylated protein accounted for 40% of the total protein. The pegylated IFN-alpha was purified from the 60 minute reaction mixture and characterized using hydrophobic exchange chromatography (Bio-Rad; Biogel-phenly-S-PW). A linear gradient with decreasing salt concentrations from 0.42M to 0.0M $(NH_4)_2SO_4$ in 50 mM sodium phosphate pH 7.0 in 20 minutes was used to separate pegylated IFN-alpha and unmodified IFN-alpha. Aliquots of the fractions were evaluated by SDS-PAGE and pooled fractions were assayed for anti-viral activity (specific activity) in an MDBK assay by the method described in by Familletti, et al. [Methods Enzym. 78, 387 (1987)].

Protein concentrations were determined spectrophotometrically at 280 nM using an extinction coefficient of 1.0 for a 1 mg/ml IFN-alpha buffered solution. The specific activity of the isolated proteins is expressed as units per mg protein and the results are summarized in Table IX.

The results show that the specific activity of the 28 kD pegylated IFN-alpha was not significantly altered relative to IFN-alpha.

TABLE IX

Bioactivity of IFN-alpha Conjugated with the reagent of Example 5

| Apparent Molecular Weight of IFN-alpha Protein (kD) | Specific Activity (units/mg) |
|---|---|
| 15 (unmodified) | $1.1 \times 10^8$ |
| 28 | $1.4 \times 10^8$ |

Example 8A

Preparation on of IFN-alpha conjugated to PEG by means of the reagent alpha-[(1,2-Dihydro-2-oxo-1-pyridinyl)-thiocarbonyl]omega-methoxypoly-(oxy-1,2-ethanediyl) SRU 225.

IFN-alpha was pegylated as in example 8 with the reagent described in Example 5a. Three predominant molecular weight species from reaction mixture at 60 minutes were identified by SDS-PAGE with apparent molecular weights corresponding to 15 (unmodified), 35 and 43 kD. The latter two pegylated proteins accounted for 35 and 33 per cent of the total proteins in the reaction mixture, respectively.

The specific activities determined by procedures described in Example 8 of the pegylated species of IFN-alpha are summarized in Table X. The results show that the 35 kD pegylated IFN-alpha product retained biological activity within 2–3 fold of IFN-alpha. The 43 kD conjugate lost substantial activity.

TABLE X

Bioactivity of IFN-alpha Conjugated with the reagent of Example 5a

| Apparent Molecular Weight of IFN-alpha Protein (kD) | Specific Activity (units/mg) |
|---|---|
| 15 (unmodified) | $3.3 \times 10^8$ |
| 35 | $1.2 \times 10^8$ |
| 43 | $1.5 \times 10^7$ |

Example 8B

Preparation of rIL-2 conjugated to PEG by means of the reagent alpha-[(1,2-Dihydro-2-oxo-1-pyridinyl)-thiocarbonyl]omega-methoxypoly(oxy-1,2-ethanediyl) SRU 111.7 rIL-2 was pegylated with the reagent described in Example 5 and purified using the procedure as described in Example 3.

The predominant molecular weight species from the reaction mixture after 60 minutes were identified by SDS-PAGE with an apparent molecular weights of 15 (unmodified) and 25 kD. The 25 kD pegylated protein accounted for 60% of the total protein in the reaction.

The specific activity of the rIL-2 isolated proteins were measured as described in Example 3 and is expressed as units/mg protein and the results are summarized in Table XI.

As can be see in Table XI, the biological activity of IL-2 was not altered after conjugation with PEG.

TABLE XI

Bioactivity of rIL-2 Conjugated to PEG with the reagent described in Example 5

| Apparent Molecular Weight of rIL-2 Protein (kD) | Specific Activity (units/mg) |
|---|---|
| 15 (unmodified) | $2.0 \times 10^7$ |
| 25 | $2.0 \times 10^7$ |

Example 8C

Preparation of rIL-2 conjugated to PEG by means of the reagent alpha-[(1,2-Dihydro-2-oxo-1-pyridinyl)-thiocarbonyl]omega-methoxypoly(oxy-1,2-ethanediyl) SRU 225 rIL-2 was pegylated using the procedure described in Example 3 with the reagent described in Example 5a.

The predominant molecular weight species from the reaction mixture after 60 minutes were identified by SDS-PAGE with apparent molecular weights of 15 kD (unmodified), 33 kD, and 43 kD. The 33 and 43 kD pegylated proteins accounted for 60 and 20 per cent of the total protein in the reaction, respectively.

EXAMPLE 9

Preparation of IFN-alpha conjugated to PEG by means of the reagent alpha-[(1,2-Dihydro-2-oxo-1-pyridinyl)-thiocarbonyl]-omega-methoxy-poly(oxy-1,2-ethanediyl) SRU 111.7.

An alternative method for conjugating IFN-alpha to PEG was done as follows:

IFN-alpha (5 mg in 1 ml) was dialyzed against a buffer containing 5 mM sodium acetate, pH 5.0, 120 mM NaCl. To the dialyzed protein solution, solid potassium thiocyanate was added to obtain a final concentration of 0.5M salt, and the pH adjusted by the addition of one-tenth volume of 1M tricine-sodium hydroxide, pH 11.9 to give a final pH 10.0 solution. alpha-[(1,2-Dihydro-2-oxo-1-pyridinyl) thiocarbonyl]-omega-methoxypoly(oxy-1,2-ethanediyl) was added to the sample at a molar ratio of 3 moles of reagent to 1 mole of protein. The modification reaction was allowed to proceed at room temperature for 30 minutes, and stopped by the addition of 1M glycine, pH 6.3 to a final concentration of 20 mM. PEG-modified protein was precipitated from solution by addition of a buffer containing 3.5M ammonium sulfate, 50 mM sodium phosphate, pH 7.0 to a final concentration of 1.1M ammonium sulfate and the precipitate collected by centrifugation (10,000×g for 12 min.). After rinsing the pellet with a buffer containing 1.1M ammonium sulfate, 50 mM sodium phosphate, pH 7.0, the pellet was redissolved in a buffer containing 25 mM ammonium acetate, pH 5.0. The PEG-modified protein was purified and characterized as described in Example 2. A single pegylated IFN species was obtained with an apparent molecular weight of 28 kD. Antiviral activity (specific activity) of the modified protein was determined by the procedure described in Example 8. The specific activity of the starting IFN-alpha was $2.6 \times 10^8$ U/mg and the specific activity of the IFN-alpha conjugated to PEG was $1.0 \times 10^8$ U/mg demonstrating that the PEG conjugated IFN-alpha retained biological activity within 3-fold relative to IFN-alpha.

EXAMPLE 10

Preparation of IFN-alpha conjugated to PEG by means of the reagent alpha-[(1,2-Dihydro-2-oxo-1-pyridinyl)-thiocarbonyl]-omega-methoxypoly(oxy-1,2-ethanediyl) SRU 225.

IFN-alpha was conjugated to PEG according to the procedure described in Example 9. The proteins were purified and characterized as described in Examples 2 and 9. The starting IFN-alpha had a specific activity of $2.6 \times 10^8$ U/mg using the IFN-alpha conjugated to PEG which has an apparent molecular weight of 31 kD and had a specific activity of $1.0 \times 10^8$ U/mg as described in Example 8. The bioactivity of the conjugated IFN-alpha was within 3-fold of IFN-alpha.

EXAMPLE 11

Preparation of alpha-Methyl-omega-[2-[[(2-pyridinyloxy) carbonyl]amino]ethoxy]poly(oxy-1,2-ethanediyl) SRU 111.7.

From a solution of 1 g (0.2 mmol) of alpha-(2-aminoethyl)-omega-methoxypoly (oxy-1,2-ethanediyl) SRU 111.7 (as prepared in Example 1C) in 40 ml of dry $CH_2Cl_2$ was distilled 15 ml of solvent. To the resulting solution at 0° C. was then added 65 mg (0.3 mmol) of di-2-pyridyl carbonate and the mixture stirred for an additional 4 hours. The solvent was then removed under reduced pressure and the residue triturated with diethyl ether. The precipitate was then filtered and washed with 50 ml of ether followed by 50 ml of hexane. The product was then dried in a vacuum oven under a slow stream of nitrogen to give 1 g of alpha-methyl-omega-[2-[[(2-pyridinyloxy)carbonyl] amino]ethoxy]poly(oxy-1,2-ethanediyl) SRU 111.7. as a white powder.

Anal. Calcd for $C_9H_{12}N_2O_3(CH_2CH_2O)_{111.7}$: C, 54.56; H, 9.04; N, 0.55; Found: C, 54.26; H, 9.00; N, 0.53.

Example 11a

Preparation of alpha-Methyl-omega-[2-[[(2-pyridinyloxy) carbonyl]amino]ethoxy]poly(oxy-1,2-ethanediyl) SRU 225

By the procedure described in Example 11, alpha-(2-aminoethyl)-omega-methoxypoly (oxy-1,2-ethanediyl) SRU 225, (as prepared in Example 1c) was converted to alpha-methyl-omega-[2-[[(2-pyridinyloxy)carbonyl]amino] ethoxy]poly(oxy-1,2-ethanediyl) SRU 225.

Anal. Calcd for $C_9H_{12}N_2O_3(CH_2CH_2O)_{225}$: C, 54.54, H, 9.10; N, 0.28. Found: C, 54.49; H, 9.27; N, 0.31.

Example 11b

Preparation of alpha-Methyl-omega-[2-[[(2-pyridinyloxy) carbonyl]amino]ethoxy]poly(oxy-1,2-ethanediyl) SRU 28.3

By the procedure described in Example 11, alpha-(2-amino-ethyl)-omega-methoxypoly (oxy-1,2-ethanediyl) SRU 28.3 (as prepared in Example 1f) was converted to alpha-methyl-omega-[2-[[(2-pyridinyloxy)carbonyl]-amino]ethoxy]poly(oxy-1,2-ethanediyl) SRU 28.3.

Anal: Calcd for $C_9H_{12}N_2O_3(CH_2CH_2O)_{28.3}$: C, 54.61; H, 8.75; N, 1.94. Found: C, 54.67; H, 8.96; N, 1.63.

EXAMPLE 12

Preparation of IL-1ra conjugated to PEG by means of the reagent alpha-Methyl-omega-[2-[[(2-pyridinyloxy)-carbonyl]amino]ethoxy]poly(oxy-1,2-ethanediyl), SRU 111.7 alpha-Methyl-omega-[2-[[(2-pyridinyloxy)carbonyl] amino]-ethoxy]poly(oxy-1,2-ethanediyl) SRU 111.7, was added to 25 mg of purified IL-1ra in 2.5 ml of buffer (0.1M sodium borate, pH 9.0) in a molar ratio of 1 mole of reagent per one mole of IL-1ra. The solutions were thoroughly mixed and the pegylation reaction was allowed to proceed at room temperature for 60 minutes. PEG modified ILra was then purified according to the procedure set out in Example 6.

The predominant pegylated products from the 60 minute reaction had apparent molecular weights of 28 kD and 38 kD and accounted for approximately 42 and 29% of the total protein from the reaction mixture, respectively.

The ability of the purified IL-1ra proteins from the reaction mixture to inhibit IL-1 binding was determined as described in Example 6 and summarized in Table XII. The binding properties of the 28 kD product was not significantly altered and the bindability of the 38 kD protein retained activity within 5-fold of IL-1ra.

TABLE XII

Inhibition of [¹²⁵I]-IL-1 Binding by IL-1ra Protein Pegylated with the reagent described in Example 11

| Apparent Molecular Weight of IL-1ra Protein (kD) | $IC_{50}$ (ng/ml) |
|---|---|
| 19 (unmodified) | 2.0 |
| 28 | 3.0 |
| 38 | 10.0 |

The pharmacodynamic profile of PEG-IL-1ra was determined as described in Example 6. The data are summarized in Table D3. IL-1 alone induced 27283 u/ml of IL-6. Unmodified IL-1ra inhibited less than 50% of the IL-1 response within 6 hours of administration. In contrast, PEG IL-1ra although less active at early time points, was much more active at 24 and 48 hours after injection. Thus, the PEG-IL-1ra exhibited a prolonged pharmacodynamic profile.

TABLE D3

Pharmacodynamic Profile of IL-1ra Conjugated with the reagent described in Example 11

| Time (hr.) Prior to IL-1 Administration | IL-6 Units/ml | |
|---|---|---|
| | 19 kD | 26kD |
| 0 | 4789 | 23806 |
| 6 | 15324 | 10833 |
| 24 | 24841 | 5727 |
| 48 | 16348 | 9364 |
| 72 | 12067 | 12054 |

Example 12A

Preparation of IL-1ra conjugated to PEG by means of the reagent alpha-Methyl-omega-[2-[[(2-pyridinyloxy)-carbonyl]amino]ethoxy]poly(oxy-1,2-ethanediyl), SRU 225 alpha-Methyl-omega-[2-[[(2-pyridinyloxy)carbonyl]amino]-ethoxy]poly(oxy-1,2-ethanediyl) SRU 225, (previously described in Example 11a) was added to 25 mg of purified IL-1ra in 2.5 ml of buffer (0.1M sodium borate, pH 9.0) in a molar ratio of 4 moles of reagent per one mole of IL-1ra. The solutions were thoroughly mixed and the pegylation reaction was allowed to proceed at room temperature for 60 minutes. PEG modified IL-1ra was then purified according to the procedure set out in Example 6.

The predominant pegylated products from the 60 minute reaction had apparent molecular weights of 33 kD and 48 kD and accounted for approximately 76 and 15% of the total protein from the reaction mixture respectively. The ability of the purified IL-1ra proteins from the reaction mixture to inhibit IL-1 binding are summarized in Table XIII. The 33 kD PEG modified protein retained its ability to inhibit IL-1 binding within 8-fold relative to IL-1ra. The 48 kD product lost substantial binding capacity.

TABLE XIII

Inhibition of [¹²⁵I]IL-1 Binding by IL-1ra Proteins Pegylated with the reagent described in Example 11a

| Apparent Molecular Weight of IL-1ra Protein (kD) | $IC_{50}$ (ng/ml) |
|---|---|
| 19 (unmodified) | 0.8 |
| 33 | 6.0 |
| 48 | 18.0 |

The pharmacokinetic profile of PEG-IL-1ra was determined as described in Example 6A. The data are summarized in Table D4. The PEG-IL-1ra was detectable in serum samples at higher concentrations and for a prolonged time compared to the unmodified IL-1ra.

TABLE D4

Pharmacokinetic Profile of IL-1ra Conjugated with the reagent described in Example 11a

| Time (hr.) After Administration | Serum Level of IL-1ra (ng/ml) | |
|---|---|---|
| | 19 kD | 33 kD |
| 1 | 220 | |
| 2 | 33 | 700 |
| 3 | 13 | |
| 4 | 5.3 | 500 |
| 6 | 1.5 | |
| 8 | | 150 |
| 10 | | 83 |
| 24 | | 5 |

EXAMPLE 13

Preparation of rIL-2 conjugated to PEG by means of the reagent alpha-Methyl-omega-[2-[[(2-pyridinyloxy)-carbonyl]amino]ethoxy]poly(oxy-1,2-ethanediyl), SRU 111.7 rIL-2 was pegylated with alpha-methyl-omega-[2-[[(2-pyridinyloxy)carbonyl]amino]ethoxy]poly(oxy-1,2-ethanediyl), SRU 111.7, according to the procedure set forth in Examples 3 and 8b. The specific activity of the IL-2 protein was determined as described in Example 8. The specific activity of the 15 kD unmodified rIL-2 was $2 \times 10^7$ units/mg and of the 29 kD pegylated IL-2 was $2.4 \times 10^7$ units/mg IL-2 indicating no substantial loss of biological activity as a result of pegylation.

EXAMPLE 14

Preparation of PEG-modified rIL-1 alpha conjugated to PEG by means of the reagent alpha-Methyl-omega-[2-[[(2-pyridinyloxy)carbonyl]amino]ethoxy]poly(oxy-1,2-ethanediyl), SRU 111.7 rIL-1 alpha was pegylated with the reagent described in Example 11, alpha-methyl-omega-[2-[[(2-pyridinyloxy)-carbonyl]amino]ethoxy]poly(oxy-1,2-ethanediyl) SRU 111.7, according to the procedure set forth in Examples 4 and 7. Two pegylated rIL-1 alpha proteins with apparent molecular weights of 28 kD and 38 kD were purified and accounted for 50 and 25 per cent of the total proteins from the reaction mixture at 60 minutes respectively.

EXAMPLE 15

Preparation of IFN-alpha conjugated to PEG by means of the reagent alpha-Methyl-omega-[2-[[(2-pyridinyloxy)-carbonyl]amino]ethoxy]poly(oxy-1,2-ethanediyl), SRU 111.7

IFN-alpha was pegylated with the reagent described in Example 11, alpha-methyl-omega-[2-[[(2-pyridinyloxy)carbonyl]amino]-ethoxy]poly(oxy-1,2-ethanediyl) SRU 111.7, according to the procedure set forth in Example 8. Forty percent of the protein was derivatized after 60 minutes and the product had an apparent molecular weight of 26 kD.

EXAMPLE 16

Preparation of IFN-alpha conjugated to PEG by means of the reagent alpha-Methyl-omega-[2-[[(2-pyridinyloxy)-carbonyl]amino]ethoxy]poly(oxy-1,2-ethanediyl), SRU 111.7 Alternative method of peyglating IFN-alpha.

Using the procedure illustrated in Example 9, IFN-alpha was conjugated to PEG by alpha-methyl-omega-[2-[[(2-pyridinyloxy)-carbonyl]amino]ethoxy]poly(oxy-1,2-ethanediyl), SRU 111.7. The specific activity of IFN-alpha was determined as described in Example 8. The specific activity of the starting IFN-alpha was $1.7 \times 10^8$ U/mg and the specific activity of the IFN-alpha conjugated to PEG by alpha-methyl-omega-[2-[[(2-pyridinyloxy)carbonyl]-amino]ethoxy]poly(oxy-1,2-ethanediyl) was $0.8 \times 10^8$ U/mg which is within 2–3 fold of the IFN-alpha.

EXAMPLE 17

Preparation of IFN-alpha conjugated to PEG by means of the reagent alpha-Methyl-omega-[2-[[(2-pyridinyloxy)-carbonyl]amino]ethoxy]poly(oxy-1,2-ethanediyl) SRU 225.

Using the procedure illustrated in Example 9, IFN-alpha was pegylated by means of the reagent described in Example 11a. The specific activity as determined by the method described in Example 8 of the IFN-alpha conjugated to PEG was $0.4 \times 10^8$ U/mg demonstrating no significant loss in bioactivity.

EXAMPLE 18

Preparation of alpha-[(2-Pyridinyloxy)carbonyl] omega-methoxypoly (oxy-1,2-ethanediyl) SRU 111.7

From a solution of 1 g MPEG molecular weight 5000 dissolved in 30 ml of dry $CH_2Cl_2$ was distilled 10 ml of solvent. The solution was cooled to room temperature and 132 mg (0.6 mM) of di-2-pyridyl carbonate and 4 mg of DMAP were added. The resulting solution was then stirred for 14 hours and the solvent removed under vacuum. The residue was triturated with diethyl ether and the resulting precipitate filtered. The product was then dissolved in 7 ml of dry glyme, warmed to cause dissolution, and the resulting solution allowed to cool and stand at room temperature for several hours. The resulting precipitate was then filtered and washed with 2×5 ml of dry glyme. The solid was then dried in a vacuum oven and under a stream of nitrogen to give 0.7 g of alpha-[(2-pyridinyloxy)-carbonyl]omega-methoxypoly (oxy-1,2-ethanediyl) SRU 111.7.

Anal. Calcd for $C_9H_{11}NO_4(CH_2CH_2O)_{111.7}$: C, 54.57; H, 9.02; N, 0.28. Found: C, 54.51; H, 9.19; N, 0.28.

Example 18a

Preparation of alpha-[(2-Pyridinyloxy)carbonyl] omega-methoxypoly (oxy-1,2-ethanediyl), SRU 225

By the procedure described in Example 18, MPEG (methoxypolyethylene glycol) molecular weight 10,000 was converted to alpha-[(2-pyridinyloxy)carbonyl]omega-methoxypoly (oxy-1,2-ethanediyl), SRU 225.

Anal. Calcd for $C_9H_{11}NO_4(CH_2CH_2O)_{225}$: C, 54.54; H, 9.08; N, 0.14. Found: C, 54.54; H, 9.12; N, 0.11.

EXAMPLE 19

Preparation of IL-1ra conjugated to PEG by means of the reagent alpha-[(2-Pyridinyloxy)carbonyl] omega-methoxypoly (oxy-1,2-ethanediyl), SRU 111.7

IL-1ra was pegylated with alpha-[(2-pyridinyloxy) carbonyl]-omega-methoxypoly (oxy-1,2-ethanediyl), SRU 111.7 by the procedure previously described in Examples 6 and 12. The predominant pegylated products had apparent molecular weights of 26 kD and 33 kD and accounted for approximately 31 and 57 per cent of the total protein from the 60 minute reaction mixture, respectively. The ability of the purified IL-1ra proteins from the reaction mixture to inhibit IL-1 binding was determined as described in Example 6 and summarized in Table XIV. The 26 kD pegylated IL-1ra conjugate retained its binding capacity within 4-fold of IL-1ra. The 33 kD conjugate lost significant binding activity as indicated by a 15-fold decrease in competitive binding activity.

TABLE XIV

Inhibition of [$^{125}$I]IL-1 Binding by IL-1ra Proteins Pegylated with the reagent described in Example 18

| Apparent Molecular Weight of IL-1ra Protein (kD) | $IC_{50}$ (ng/ml) |
|---|---|
| 19 (unmodified) | 2.0 |
| 26 | 8.0 |
| 33 | 30.0 |

Example 19A

Preparation of IL-1ra conjugated to PEG by means of the reagent alpha-[(2-Pyridinyloxy)carbonyl] omega-methoxypoly (oxy-1,2-ethanediyl), SRU 225

IL-ra was pegylated with alpha-[(2-pyridinyloxy) carbonyl]omega-methoxypoly (oxy-1,2-ethanediyl), SRU 225, according to the procedure set forth in Example 19. The predominant pegylated products from the 60 minute reaction method mixture had apparent molecular weights of 33 kD and 48 kD and accounted for approximately 47 and 25 per cent of the total protein from the reaction mixture, respectively.

The ability of the purified IL-1ra proteins from the reaction mixture to inhibit IL-1 binding was determined as described in Examples 6 and 12 and summarized in Table XV. The 33 kD protein retained activity within 6-fold of IL-1ra. The higher molecular weight conjugate lost significant activity.

TABLE XV

Inhibition of [$^{125}$I]IL-1 Binding by IL-1ra Proteins
Pegylated with the reagent described in Example 18a

| Apparent Molecular Weight of IL-1ra Protein (kD) | IC$_{50}$ (ng/ml) |
|---|---|
| 19 (unmodified) | 1.5 |
| 33 | 9.0 |
| 48 | 40.0. |

The pharmacokinetic profile of PEG-IL-1ra was determined as described in Example 6A. The data are summarized in Table D5. The PEG-IL-1ra was detectable in the serum samples for a prolonged time compared to the unmodified IL-1ra demonstrating a prolonged serum half-life. The pharmacodynamic profile of PEG-IL-1ra was determined as described in Example 6, except that 0.05 ug of rIL-1 alpha was administered. The data are summarized in Table D6. The response to IL-1 alone was 9203 units/ml IL-6. A prolonged inhibitory effect, compared to unmodified IL-1ra, can be seen at up to 72 hours following administration of the PEG-IL-1ra demonstrating improved pharmacodynamic properties. Collectively, these data illustrate that even if a pegylated protein has diminished activity in vitro, it could have improved pharmaco-dynamic properties in vivo.

TABLE D5

Pharmacokinetic Profile of IL-1ra Conjugated
with the reagent described in Example 18a

| | Serum IL-1ra (ng/ml) | |
|---|---|---|
| Time (hr.) After Administration | 19 kD | 33 kD |
| 1 | 580 | |
| 2 | 75 | 100 |
| 3 | 30 | |
| 4 | 30 | 60 |
| 6 | 8 | |
| 8 | | 12 |
| 10 | | 17 |
| 24 | | 10 |

TABLE D6

Pharmacodynamic Profile of IL-1ra Conjugated
with the reagent described in Example 18

| Time (hr.) Prior to | IL-6 (Units/ml) | |
|---|---|---|
| IL-1 Administration | 19 kD | 26 kD |
| 0 | 521 | 454 |
| 6 | 2334 | 416 |
| 24 | 13486 | 2552 |
| 48 | 16577 | 4667 |
| 72 | 12800 | 5148 |

EXAMPLE 20

Preparation of IFN-alpha conjugated to PEG by means of the reagent alpha-[(2-Pyridinyloxy) carbonyl]omega-methoxypoly (oxy-1,2-ethanediyl), SRU 111.7

The reagent alpha-[(2-pyridinyloxy)carbonyl]omega-methoxypoly (oxy-1,2-ethanediyl), SRU 111.7, was added to 1 mg of purified IFN-alpha in 200 ul of buffer (0.1 sodium borate, pH 9.0) in a molar ratio of 10 moles of reagent per mole IFN-alpha. The solutions were thoroughly mixed and the pegylation reaction was allowed to proceed at room temperature for 60 minutes. Purified PEG-modified IFN-alpha was then obtained according to the procedure set forth in Example 8. Thirty-six percent of the protein was derivatized and the product had an apparent molecular weight of 28 kD.

The specific activity of the purified IFN proteins from the reaction mixture were determined as described in Example 8 and the values are summarized in Table XVI. The modified IFN had a 5–6 fold decrease in biological activity in vitro.

TABLE XVI

Bioactivity of IFN-alpha Conjugated with the reagent
described in Example 18

| Apparent Molecular Weight of IFN-alpha Protein (kD) | Specific Activity units/mg |
|---|---|
| 15 (unmodified) | $1.88 \times 10^8$ |
| 28 | $8.0 \times 10^7$ |

Example 20A

Preparation of rIL-2 conjugated to PEG by means of the reagent alpha-[(2-Pyridinyloxy)carbonyl] omega-methoxypoly (oxy-1,2-ethanediyl), SRU 111.7

The reagent alpha-[(2-pyridinyloxy)carbonyl]omega-methoxypoly (oxy-1,2-ethanediyl), SRU 111.7, previously described in Example 18, was added to 1 mg of rIL-2 in 200 ul of buffer (0.1 sodium borate, pH 9.0) in a molar ratio of 5 moles of the reagent per one mole of rIL-2. The solutions were thoroughly mixed and the pegylation reaction was allowed to proceed at room temperature for 60 minutes.

The predominant molecular weight species from the 60 minute reaction mixture were identified by SDS-PAGE with apparent molecular weights of 15 kD (unmodified) and 25 kD. The 25 kD pegylated protein accounted for 60% of the total protein.

EXAMPLE 21

Preparation of IFN alpha conjugated to PEG by means of the reagent alpha-[(2-Pyridinyloxy) carbonyl]omega-methoxypoly (oxy-1,2-ethanediyl) SRU 111.7.

IFN-alpha was pegylated with the reagent described in Example 18 according to the procedure described in Example 9.

The specific activity as determined by methods described in Example 8, of the starting unmodified IFN-alpha was $1.0 \times 10^8$ U/mg and the specific activity of the IFN-alpha conjugated to PEG was $0.4 \times 10^8$ U/mg demonstrating no significant loss in bioactivity.

EXAMPLE 22

Preparation of IFN alpha conjugated to PEG by means of the reagent alpha-[(2-Pyridinyloxy) carbonyl[omega-methoxypoly (oxy-1,2-ethanediyl) SRU 225.

PEG was conjugated to IFN-alpha using the reagent described in Example 18a with the procedures of Example 9. The specific activity as determined by methods described in Example 8 of the IFN-alpha conjugated to PEG was $0.3 \times 10^8$ U/mg.

EXAMPLE 23

Preparation of alpha-[2-(Isothiocyanato)ethyl]-omega-methoxypoly (oxy-1,2-ethanediyl) SRU 111.7

To 2 g of alpha-(2-aminoethyl)-omega-methoxypoly (oxy-1,2-ethanediyl) SRU 111.7 in 100 ml $CH_2Cl_2$ was added 94.2 mg of di-2-pyridylthionocarbonate. The solution was allowed to stir 18 hours and then extracted with a small amount of cold water. Most of the $CH_2Cl_2$ was removed under reduced pressure and ether added to cause precipitation. The product was filtered and dried under high vacuum to give alpha-[2-(isothiocyanato)ethyl]-omega-methoxypoly (oxy-1,2-ethanediyl) SRU 111.7.

Anal. Calcd for $C_4H_7NOS$ $(CH_2CH_2O)_{111.7}$: C, 53.88; H, 9.07; N, 0.28; S, 0.64. Found: C, 54.45; H, 8.93; N, 0.28; S, 0.53.

EXAMPLE 24

Preparation IFN-alpha conjugated to PEG by means of the reagent alpha-[2-(Isothiocyanato)ethyl]-omega-methoxypoly (oxy-1,2-ethanediyl), SRU 111.7

The reagent alpha-[2-(isothiocyanato)ethyl]-omega-methoxypoly (oxy-1,2-ethanediyl), SRU 111.7, previously described in Example 23 was added to 1 mg of purified IFN-alpha in 200 ul of buffer (0.1M sodium borate, pH 9.0) in a molar ratio of 10 moles of reagent per one mole IFN-alpha. The solutions were thoroughly mixed and the pegylation reaction was allowed to proceed at room temperature for 60 minutes. Thirty percent of the product was derivatized and had an apparent molecular weight of 26 kD.

EXAMPLE 25

Preparation of rIL-2 conjugated to PEG by means of the reagent alpha-[2-(Isothiocyanato)ethyl]-omega-methoxypoly (oxy-1,2-ethanediyl), SRU 111.7

The reagent alpha-[2-(isothiocyanato)ethyl]-omega-methoxypoly (oxy-1,2-ethanediyl) SRU 111.7, previously described in Example 23, was added to 1.0 mg of recombinant IL-2 (rIL-2) in 100 ul of buffer (0.1M sodium borate, pH 9.0) in a molar ratio of 10 moles of reagent PEG per mole rIL-2. The solutions were thoroughly mixed and the pegylation reaction was allowed to proceed at room temperatures for 60 minutes. Purified PEG-modified rIL-2 was then obtained according to the procedure as set forth in Example 3. The derivatization results are summarized in Table XVII.

TABLE XVII

Modification of rIL-2 with the reagent described in Example 23

| Apparent Molecular Weight of rIL-2 Protein (kD) | % of Total Protein from Reaction |
|---|---|
| 15 (unmodified) | 70 |
| 26 | 20 |
| 30 | 10 |

EXAMPLE 26

Preparation IL-1ra conjugated to PEG by means of the reagent alpha-[2-(Isothiocyanato)ethyl]-omega-methoxypoly (oxy-1,2-ethanediyl), SRU 111.7

IL-1ra was pegylated with alpha-[2-(isothiocyanato) ethyl]-omega-methoxypoly (oxy-1,2-ethanediyl), SRU 111.7, according to the procedure described in Example 6. The predominant pegylated products had molecular weights of 26, 31, 38 and 48 kD and accounted for approximately 17, 44, 15 and 10 per cent of the total protein, respectively.

The ability of the purified 26 kD IL-1ra protein from the 60 minute reaction mixture to inhibit IL-1 binding was determined by methods described in Example 6 and summarized in Table XVIII. The pegylated protein retained its binding capacity within 2–3 fold of IL-1ra.

TABLE XVIII

Inhibition of [$^{125}$I]IL-1 Binding by IL-1ra Protein Pegylated with the reagent described in Example 23

| Apparent Molecular Weight of IL-1ra Protein (kD) | $IC_{50}$ (ng/ml) |
|---|---|
| 19 | 2.0 |
| 26 | 5.0 |

EXAMPLE 27

Preparation of rIL-1 alpha conjugated to PEG by means of the reagent alpha-[2-(Isothiocyanato) ethyl]-omega-methoxypoly (oxy-1,2-ethanediyl), SRU 111.7

Recombinant IL-1 alpha was pegylated with alpha-[2-(isothiocyanato)ethyl]-omega-methoxypoly (oxy-1,2-ethanediyl), SRU 111.7, as described in Example 4. Two predominant molecular weight pegylated species from the 60 minute reaction mixture were identified by SDS-PAGE with apparent molecular weights of 26 and 38 kD. The latter two pegylated proteins accounted for 46 and 48 per cent of the total protein, respectively. The pegylated rIL-1 alpha was purified from the reaction mixture and characterized as described in Example 4.

The bioactivity of the pooled purified fractions were evaluated in the D10 cell proliferation assay as described in Example 7 and results summarized in Table XIX. The samples noted as mixtures in the table contained more than one protein species that was not further purified. The 26 kD pegylated protein had a specific activity essentially indistinguishable from IL-1.

TABLE XIX

Bioactivity of rIL-1 alpha conjugated to PEG with the reagent described in Example 23

| Apparent Molecular Weight of rIL-1 alpha Protein (kD) | Specific Activity units/mg |
|---|---|
| 17 | $1.1 \times 10^8$ |
| 26 | $1.7 \times 10^8$ |
| 26, 38 (mixture) | $2.0 \times 10^8$ |
| >38 (mixture) | $6.0 \times 10^6$ |

EXAMPLE 28

Preparation of alpha-[(2-Pyridinyloxy)thiocarbonyl] -omega-methoxypoly (oxy-1,2-ethanediyl) SRU 225.

From a solution of 1 g (0.1 mmol) MPEG (methoxypolyethylene glycol molecular weight 10,000) in 30 ml of $CH_2Cl_2$ was distilled 10 ml of solvent. The resulting solution was cooled and 69.7 mg (0.3 mmol) of di-2-pyridyl thionocarbonate and 2 mg of DMAP added. The mixture was then stirred under an atmosphere of argon for 18 hours. The solvent was removed under vacuum and the residue redissolved in a minimum of $CH_2Cl_2$. Ether was then added and the resulting precipitate filtered and washed with ether. The product was then dissolved in 5 ml of warm glyme and the resulting solution allowed to stand overnight. The resulting precipitate was then filtered and washed with 2×5 ml of glyme and 5 ml of diethyl ether. The product was then dried in a vacuum oven under a slow stream of nitrogen to give 0.9 g of alpha-[(2-pyridinyloxy)thio-carbonyl]-omega-methoxypoly (oxy-1,2-ethanediyl) SRU 225.

Anal. Calcd for $C_9H_{11}NO_3S(CH_3CH_2O)_{225.3}$: C, 54.46; H, 9.04. Found: C, 54.67; H, 9.30.

EXAMPLE 29

Preparation of IL-1ra conjugated to PEG by means of the reagent alpha-[(2-Pyridinyloxy)thiocarbonyl]-omega-methoxypoly (oxy-1,2-ethanediyl), SRU 225 alpha-[(2-Pyridinyloxy)thiocarbonyl]-omega-methoxypoly (oxy-1,2-ethanediyl), SRU 225, prepared as described in Example 28, was added to 2.0 mg of IL-1ra in 1.0 ml of buffer (0.1M sodium borate, pH 9.0) in a molar ratio of 2 moles of the reagent per one mole of IL-1ra. The solutions were thoroughly mixed and the pegylation reaction was allowed to proceed at room temperature for 60 minutes. PEG modified IL-1ra was then purified according to the procedure set out in Example 6.

The predominant pegylated product had an apparent molecular weight of 33 kD and accounted for approximately 17% of the total protein from the 60 minute reaction mixture. The ability of the purified IL-1ra proteins from the reaction mixture to inhibit IL-1 binding was determined as described in Example 6 and summarized in Table XX. The binding capacity of the 33 kD protein was within 3–4 fold of the IL-1ra.

TABLE XX

Inhibition of [$^{125}$I]IL-1 Binding by IL-1ra Proteins pegylated with the reagent described in Example 28

| Molecular Weight of IL-1ra Protein (kD) | $IC_{50}$ (ng/ml) |
|---|---|
| 19 (unmodified) | 1.4 |
| 33 | 5.0 |

EXAMPLE 30

Carbonothioic acid o,o-di-(6-methyl-2-pyridinyl) ester

To a solution of 10 g (0.09 mol) of 6-methyl-2-hydroxypyridine in 250 ml of dry $CH_2Cl_2$ was added 12.7 ml of triethylamine. The solution was cooled to 0° C. and under an atmosphere of argon was added dropwise 4.1 ml (0.046 mol) of a solution of thiophosgene in $CCl_4$ (85%). The mixture was then allowed to stir at room temperature for 5 hr., filtered and the $CH_2Cl_2$ solution washed twice with 100 ml of a saturated $NaHCO_3$ solution. The organic layer was dried and the solvent removed under reduced pressure. Hexane (100 ml) was then added to the residue and the resulting mixture was allowed to digest overnight. The resulting precipitate was filtered, washed with hexane and dried in a vacuum oven under a slow stream of nitrogen to give 5.7 g of carbonothioic acid o,o-di-(6-methyl-2-pyridinyl) ester m.p. 155°–156° C.

Anal. Calcd for $C_{13}H_{12}N_2O_2S$: C, 59.98; H, 4.65; N, 10.76; S, 12.32. Found: C, 59.65; H, 4.59; N, 10.75; S, 12.06.

EXAMPLE 31 alpha-Methyl-omega-[2-[[(6-methyl-2-pyridinyloxy) thiocarbonyl]amino]ethoxy]poly(oxy-1,2-ethanediyl) SRU 225

A solution of 1 g of alpha-methoxy-omega-(2-aminoethyl) poly(oxy-1,2-ethanediyl) SRU 225 (as prepared in Example 1c) and 52.7 mg of carbonothioic acid o,o-di (6-methyl-2-pyridinyl)ester (Example 30) dissolved in 15 ml of dry $CH_2Cl_2$ was stirred overnight at room temperature. The solvent was removed under reduced pressure and the residue triturated with diethyl ether. The precipitate was filtered and washed with ether. The product was then dissolved in 5 ml of warm glyme and filtered through a 0.75 micron Millipore filter. The solution was then allowed to stand at room temperature for 48 hr. and the resulting precipitate filtered. The product was then dried in a vacuum oven under an atmosphere of $N_2$ for 18 hr. to give 0.9 g of alpha-methyl-omega-[2-[[(6-methyl-2-pyridinyloxy) thiocarbonyl]amino]ethoxy]poly(oxy-1,2-ethanediyl) SRU 225.

Anal. Calcd for $C_{10}H_{14}N_2O_2S(CH_2CH_2O)_{225}$: C, 54.50; H, 9.09; N, 0.27; S, 0.32. Found: C, 54.38; H, 9.20; N, 0.21; S, 0.37.

EXAMPLE 32

Preparation rIL-1ra Conjugated to PEG by means of the reagent alpha-Methyl-omega-[2-[[(6-methyl-2-pyridinyloxy)thiocarbonyl]amino]ethoxy]poly (oxy-1,2-ethanediyl) SRU 225

The reagent prepared as previously described in Example 31 was added to 5.0 mg of purified rIL-1ra in 1.0 ml 0.1M sodium borate, pH 9.0 in a molar ratio of 2.0 moles reagent per mole rIL-1ra. The solution was thoroughly mixed and the reaction mixture was allowed to proceed at room temperature for 60 minutes.

The rIL1ra products were evaluated using the procedure described in Example 6. Table XXI shows the percent of modification of primary molecular weight species from the reaction mixture.

TABLE XXI

Modification of rIL-1ra with the reagent described in Example 31

| Apparent Molecular Weight of rIL-1ra Protein (kD) | % of Total Protein from Reaction |
|---|---|
| 19 (unmodified) | 30.0 |
| 35 | 65.0 |
| 48 | 5.0 | rIL-1ra products from the reaction mixture were purified using the method described in Example 6.

Purified fractions from the reaction mixture were assayed in an rIL-1 radioreceptor competition binding assay as described previously in Example 6. The results are shown in Table XXII. These results show that the 35 kD protein was 6-fold less active than unmodified IL-1ra for inhibiting II-1 binding while the 48 kD protein was 20-fold less active.

TABLE XXII

Inhibition of [$^{125}$I]IL-1 binding by rIL-1ra conjugated with the reagent described in Example 31

| Apparent Molecular Weight of rIL-1ra Protein (kD) | IC$_{50}$ (ng/ml) |
| --- | --- |
| 19 (unmodified) | 1.5 |
| 35 | 9.0 |
| 48 | 30.0 |

EXAMPLE 33 alpha-[2-[[(2-Pyridinyloxy)carbonyl]amino]ethyl]-omega-[2-[[(2-pyridinyloxy)carbonyl]amino]-ethoxy]poly(oxy-1,2-ethanediyl) SRU 180

A. Preparation of alpha-(2-Chloroethyl)-omega-(2-chloroethoxy)-poly(oxy-1,2-ethanediyl) SRU 180

From a slurry of 80 g MPEG (polyethylene glycol-molecular weight 8000) in 750 ml of toluene was distilled 200 ml of the solvent. To the refluxing solution was added dropwise 1.7 ml of dry pyridine and 4.7 ml of thionyl chloride. After refluxing for twelve hours the reaction was allowed to stir overnight. Methylene chloride (50 ml) was then added and the resulting solution filtered through 60 g of basic alumina (Wolem Super 1). The column was then eluted with 500 ml of CH$_2$Cl$_2$, the organic layers combined, and the solvent removed under reduced pressure. The residue was then dissolved in 300 ml of CH$_2$Cl$_2$ and ether slowly added while the solvents are removed on a steam bath. This procedure is continued until a cloudy suspension develops. The resulting mixture is then stirred at room temperature for several hours and the product then filtered to give 73 g of alpha-(2-chloroethyl)-omega-(2-chloro-ethoxy)-poly(oxy-1,2-ethanediyl) SRU 180.

Anal. Calcd for C$_2$H$_4$Cl$_2$(CH$_2$CH$_2$O)$_{180}$: C, 54.16; H, 9.09; Cl, 0.88. Found: C, 53.40; H, 8.81; Cl, 0.93.

B. Preparation of alpha-(2-Azidoethyl)-omega-(2-azidoethoxy)-poly(oxy-1,2-ethanediyl) SRU 180

A mixture of 72 g of alpha-(2-chloroethyl)-omega-(2-chloroethoxy)poly(oxy-1,2-ethanediyl) SRU 180, 25 g sodium azide and 700 ml of dry DMF was stirred and heated at 125° C. for 12 hours. The solvent was then removed under high vacuum and the residue dissolved in one liter of CH$_2$Cl$_2$ and filtered through Celite. The CH$_2$Cl$_2$ was then removed on a steam bath while diethyl ether was added to cause precipitation. The mixture was stirred overnight and then filtered. The precipitate was then dissolved in a minimum of glyme at 50° C., slowly cooled and filtered. The product then dried in a vacuum oven under a stream of N$_2$ to give 69 g of alpha-(2-azidoethyl)-omega-(2-azidoethoxy)-poly(oxy-1,2-ethanediyl) SRU 180.

Anal. Calcd for C$_2$H$_4$N$_6$(CH$_2$CH$_2$O)$_{180}$: C, 54.07; H, 9.08; N, 1.044. Found: C, 53.76; H, 9.28; N, 0.96.

C. Preparation of alpha-(2-Aminoethyl)-omega-(2-aminoethoxy)poly(oxy-1,2-ethanediyl) SRU 180

A solution of 69 g of alpha-(2-azidoethyl)-omega-(2-azidoethoxy)poly(oxy-1,2-ethanediyl) SRU 180 and 6.7 g (25.6 mmol) of triphenylphosphine dissolved in 200 ml of dry CH$_2$Cl$_2$ was stirred overnight under an atmosphere of argon. Water (2 ml) was added and the mixture stirred an additional 12 hours. Most of methylene chloride was removed under vacuum and 400 ml of diethyl ether added. The precipitate was filtered, washed with ether and dissolved in 300 ml of warm (50° C.) glyme. The solution was allowed to stand at room temperature overnight and the resulting precipitate filtered, washed with 2×100 ml of glyme, 2×100 ml of diethyl ether and dried in a vacuum oven under a stream of N$_2$ to give 66 g of alpha-(2-aminoethyl)-omega-(2-aminoethoxy)poly(oxy-1,2-ethanediyl) SRU 180

Anal. Calcd for C$_2$H$_8$N$_2$(CH$_2$CH$_2$O)$_{180}$: C, 54.42; H, 9.18; N, 0.35. Found: C, 53.85; H, 9.20; N, 0.43.

D. alpha-[2-[[(2-Pyridinyloxy)carbonyl]amino]ethyl]-omega-[2-[[(2-pyridinyloxy)carbonyl]amino]-ethoxy]poly(oxy-1,2-ethanediyl) SRU 180

From a solution of 1 g of alpha-(2-aminoethyl)-omega-(2-aminoethoxy)poly(oxy-1,2-ethanediyl) SRU 180 dissolved in 40 ml of dry CH$_2$Cl$_2$ was distilled 15 ml of solvent. The solution was cooled to 0° C. and 85 mg (6.39 mmol) of di-2-pyridyl carbonate added. The mixture was then stirred at 0° C. for 4 hr and the solvent removed under vacuum. The residue was triturated with diethyl ether and the product filtered and washed with ether (2×75 ml). The product was then dried under vacuum and dissolved in 8 ml of dry glyme (50° C.). The solution was then allowed to cool and stand at room temperature for 12 hr. The precipitated product was filtered, washed with 2×5 ml of glyme and dried in a vacuum oven under a stream of N$_2$ to give 1 g of alpha-[2-[[(2-pyridinyloxy)carbonyl] amino]ethyl]-omega-[2-[[(2-pyridinyloxy)carbonyl]amino]ethoxy] poly-(oxy-1,2-ethanediyl) SRU 180.

Anal. Calcd for C$_{14}$H$_{14}$N$_4$O$_4$(CH$_2$CH$_2$O)$_{180}$: C, 54.57; H, 8.99; N, 0.68. Found: C, 54.32; H, 8.79; N, 0.77.

EXAMPLE 34 alpha-[2-[[(2-Pyridinyloxy)carbonyl]amino]ethyl]-omega-[2-[[(2-pyridinyloxy)carbonyl]amino]-ethoxy]poly(oxy-1,2-ethanediyl) SRU 452

A. Preparation of alpha-(2-Chloroethyl)-omega-(2-chloroethoxy)-poly(oxy-1,2-ethanediyl) SRU 452

By the procedure described in Example 33A, polyethylene glycol molecular weight 20,000 was converted to alpha-(2-chloroethyl)-omega-(2-chloroethoxy)-poly(oxy-1,2-ethanediyl) SRU 452.

Anal. Calcd for C$_2$H$_4$Cl$_2$(CH$_2$CH$_2$O)$_{452}$: C, 54.38; H, 9.13; Cl, 0.35. Found: C, 54.36; H, 9.23; Cl, 0.40.

B. Preparation of alpha-(2-Azidoethyl)-omega-(2-azidoethoxy)-poly(oxy-1,2-ethanediyl) SRU 452

By the procedure described in Example 33B, alpha-(2-chloroethyl)-omega-(2-chloroethoxy)-poly(oxy-1,2-ethanediyl) SRU 452 was converted to alpha-(2-azidoethyl)-omega-(2-azidoethoxy)-poly-(oxy-1,2-ethanediyl) SRU 452.

Anal. Calcd for C$_2$H$_4$N$_6$(CH$_2$CH$_2$O)$_{452}$: C, 54.35; H, 9.12; N, 0.42. Found: C, 54.38; H, 9.30; N, 0.47.

C. Preparation of apha-(2-Aminoethyl)-omega-(2-aminoethoxy)poly(oxy-1,2-ethanediyl) SRU 452

By the procedure described in Example 33C, alpha-(2-azidoethyl)-omega-(2-azidoethoxy)-poly(oxy-1,2-ethanediyl) SRU 452 was converted to alpha-(2-aminoethyl)-omega-(2-aminoethoxy)poly(oxy-1,2-ethanediyl) SRU 452.

Anal. Calcd for C$_2$H$_8$N$_2$(CH$_2$CH$_2$O)$_{452}$: C, 54.49; H, 9.17; N, 0.14. Found: C, 54.44; H, 9.19; N, 0.15.

D. alpha-[2-[[(2-Pyridinyloxy)carbonyl]amino]ethyl]-omega-[2-[[(2-pyridinyloxy)car-bonyl]amino]ethoxy]poly(oxy-1,2-ethanediyl) SRU 452.

By the procedure described in Example 33D, alpha-(2-aminoethyl)-omega-(2-aminoethoxy)poly(oxy-1,2-ethanediyl) SRU 452 was converted to alpha-[2-[[(2-pyridinyloxy)carbonyl]amino]-ethyl]-omega-[2-[[(2-pyridinyloxy)car-bonyl]amino]ethoxy]poly(oxy-1,2-ethanediyl) SRU 452.

Anal. Calcd for C$_{14}$H$_{14}$N$_4$O$_4$(CH$_2$CH$_2$O)452: C, 54.56; H, 9.08; N, 0.28. Found: C, 54.33; H, 9.13; N, 0.33.

EXAMPLE 35

Preparation rIL-1ra Conjugated to PEG by means of the reagent alpha-[2-[[(2-pyridinyloxy)carbonyl]amino]ethyl]-omega-[2-[[(2-pyridinyloxy)carbonyl]amino]ethoxy]poly-(oxy-1,2-ethanediyl) SRU 452

The reagent prepared as previously described in Example 34 was added to 5.0 mg of purified rIL-1ra in 1.0 ml 0.1M sodium borate, pH 9.0 in a molar ratio of 1.0 moles of reagent per 4.0 moles rIL-1ra. The solution was thoroughly mixed at room temperature for 60 minutes.

The rIL-1ra products were evaluated using the method previously described in Example 6. Table XXIII shows the percent of modification of primary molecular weight species from the reaction mixture.

TABLE XXIII

Modification of rIL-1ra with the reagent described in Example 33

| Apparent Molecular Weight of rIL-1ra Protein (kD) | % of Total Protein from Reaction |
|---|---|
| 19 (unmodified) | 50.0 |
| 55 | 35.0 |
| 75 | 15.0 |

EXAMPLE 36

Bis-(3-Methyl-2-pyridyl)carbonate

A solution of 4.6 g (42 mmol) of 3-methyl-2-hydroxypyridine and 6 ml of triethylamine dissolved in 20 ml of CH$_2$Cl$_2$ was added dropwise at 0° C. to a solution of 50 ml of CH$_2$Cl$_2$ and 11 ml of phosgene in toluene (1.93 molar). The mixture was stirred at 0° C. for 2 hr. and then at room temperature of 2 hr. The reaction mixture was then washed with a saturated NaHCO$_3$ solution followed by a saturated NaCl solution and then dried (Na$_2$SO$_4$). The solvent was removed under reduced pressure and the residue crystallized from EtOAc/hexane to give 3 g of bis-(3-methyl-2-pyridyl) carbonate m.p. 110°–112° C.

Anal. Calcd for C$_{13}$H$_{12}$N$_2$O$_3$: C, 63.93; H, 4.95; N, 11.47. Found: C, 63.78; H, 4.86; N, 11.23.

EXAMPLE 37 alpha-Methyl-omega-[2-[[(3-methyl-2-pyridinyloxy)carbonyl]amino]ethoxy]poly(oxy-1,2-ethane-diyl) SRU 225

From a solution of 1 g of alpha-methoxy-omega-(2-aminoethyl)poly(oxy-1,2-ethanediyl) SRU 225 dissolved in 25 ml of CH$_2$Cl$_2$ was distilled 10 ml of solvent. To the solution was then added 49.2 mg (0.2 mmol) of bis-(3-methyl-2-pyridyl)carbonate and the resulting mixture stirred overnight under an atmosphere of argon. The solvent was then removed under reduced pressure and 80 ml of diethyl ether added to the residue. The solid was filtered, washed with ether and then dissolved in 10 ml CH$_2$Cl$_2$. Ether was then slowly added while boiling off the solvent until the solution becomes turbid. The mixture was then allowed to stand for 18 hr. at room temperature and the resulting precipitate filtered. The solid was then dissolved in 8 ml of warm glyme and allowed to sit at room temperature for an additional 18 hr. The product was then filtered and dried in a vacuum oven under an atmosphere of nitrogen to give 0.6 g of alpha-methyl-omega-[2-[[(3-methyl-2-pyridinyloxy)carbonyl]amino]ethoxy]poly(oxy-1,2-ethanediyl) SRU 225.

Anal. Calcd for C$_{10}$H$_{14}$N$_2$O$_3$(CH$_2$CH$_2$O)$_{225}$: C, 54.59; H, 9.09; N, 0.28. Found: C, 55.64; H, 9.14; N, 0.22.

EXAMPLE 38

Preparation rIL-1ra Conjugated to PEG by means of the reagent alpha-Methyl-omega-[2-[[(3-methyl-2-pyridinyloxy)carbonyl]amino]ethoxy]poly(oxy-1,2-ethanediyl) SRU 225

The reagent prepared as previously described in Example 37 was added to 5.0 mg of purified rIL-1ra in 1.0 ml 0.1M sodium borate, pH 9.0 in a molar ratio of 2.0 moles reagent per mole rIL-1ra. The solution was thoroughly mixed and the reaction was allowed to proceed at room temperature for 60 minutes.

The rIL-1ra products were evaluated using the procedure described in Example 6. Table XXIV shows the percent of modification of primary molecular weight species from the reaction mixture.

TABLE XXIV

Modification of rIL-1ra with the reagent described in Example 37

| Apparent Molecular Weight of rIL-1ra Protein (kD) | % of Total Protein from Reaction |
|---|---|
| 19 (unmodified) | 45.0 |
| 35 | 43.0 |
| 45 | 12.0 | rIL-1ra products from the reaction mixture were purified as described in Example 6. Purified fractions from the reaction mixture were assayed in an rIL-1 radioreceptor competition binding assay as described in Example 6. The results are shown in Table XXV. The 35 kD protein was 4-fold or less active than unmodified IL-1ra for inhibiting IL-1 binding. The 45 kD protein was 30-fold less active.

TABLE XXV

Inhibition of [$^{125}$I]IL-1 binding by rIL-1ra conjugated with the reagent described in Example 35

| Apparent Molecular Weight of rIL-1ra Protein (kD) | IC$_{50}$ (ng/ml) |
|---|---|
| 19 (unmodified) | 1.0 |
| 35 | 4.0 |
| 45 | 30.0 |

We claim:

1. A physiologically active protein conjugate of the formula

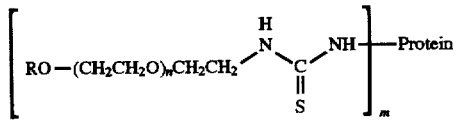

wherein R is lower alkyl; m and n form any combination of numbers such that the conjugate has at least a portion of the biological activity of the protein which forms the conjugate.

2. The protein conjugate of claim 1 wherein R is $CH_3$.

3. The protein conjugate of claim 1 wherein the protein is IL-1.

4. The protein conjugate of claim 1 wherein the protein is IL-1ra.

5. The protein conjugate of claim 1 wherein the protein is IFN-alpha.

6. The protein conjugate of claim 1 wherein the protein is IL-2.

7. A physiologically active protein conjugate of the formula

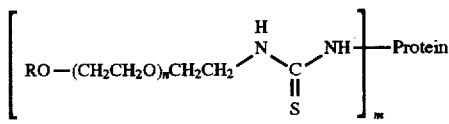

wherein R is lower alkyl; and m and n are selected from any combination of numbers such that the molecular weight of the conjugate excluding the protein is from 300 to 30,000 daltons and the conjugate has at least a portion of the biological activity of the protein which forms the conjugate.

8. The protein conjugate of claim 7 wherein R is $CH_3$.

9. The protein conjugate of claim 7 wherein the protein is IL-1.

10. The protein conjugate of claim 7 wherein the protein is IL-Ira.

11. The protein conjugate of claim 7 wherein the protein is IFN-alpha.

12. The protein conjugate of claim 7 wherein the protein is IL-2.

* * * * *